(12) United States Patent
Fukazawa

(10) Patent No.: US 9,964,497 B2
(45) Date of Patent: May 8, 2018

(54) INSPECTION METHOD, INSPECTION APPARATUS, EXPOSURE CONTROL METHOD, EXPOSURE SYSTEM, AND SEMICONDUCTOR DEVICE

(71) Applicant: Nikon Corporation, Tokyo (JP)

(72) Inventor: Kazuhiko Fukazawa, Kamakura (JP)

(73) Assignee: NIKON CORPORATION, Tokyo (JP)

( * ) Notice: Subject to any disclaimer, the term of this patent is extended or adjusted under 35 U.S.C. 154(b) by 591 days.

(21) Appl. No.: 14/528,389

(22) Filed: Oct. 30, 2014

(65) Prior Publication Data
US 2015/0049314 A1 Feb. 19, 2015

Related U.S. Application Data

(62) Division of application No. 13/325,228, filed on Dec. 14, 2011, now Pat. No. 8,945,954.

(30) Foreign Application Priority Data

Dec. 14, 2010 (JP) .................................. 2010-278308
Jan. 12, 2011 (JP) .................................. 2011-004306

(51) Int. Cl.
*H01L 21/00* (2006.01)
*G01N 21/95* (2006.01)
(Continued)

(52) U.S. Cl.
CPC ... *G01N 21/9501* (2013.01); *G01N 21/95607* (2013.01); *G02B 26/0808* (2013.01);
(Continued)

(58) Field of Classification Search
None
See application file for complete search history.

(56) References Cited

U.S. PATENT DOCUMENTS 6,313,913 B1 11/2001 Nakagawa et al.
7,643,137 B2 1/2010 Sugihara et al.
(Continued)

FOREIGN PATENT DOCUMENTS

JP H11-040476 2/1999
JP 2004-294194 10/2004
(Continued)

OTHER PUBLICATIONS

Notice of Reasons for Refusal of Japanese Patent Application No. 2012-548796 dated Apr. 21, 2015 (4 pages).
(Continued)

*Primary Examiner* — Angel Roman
(74) *Attorney, Agent, or Firm* — Finnegan, Henderson, Farabow, Garrett & Dunner, LLP

(57) ABSTRACT

There is provided an inspection apparatus which inspects a substrate supporting portion configured to support a substrate during an exposure performed by an exposure apparatus. The apparatus includes: a irradiation unit configured to irradiate, with an illumination light beam, a surface of the substrate on which a pattern has been formed by an exposure by the exposure device; a detecting unit configured to detect reflected light from a pattern in the irradiated surface; a focusing state computation unit connected to the detection unit and configured to determine a focusing state of the pattern of the substrate, based on a detection result of the reflected light beam detected by the detection unit; and an inspection unit connected to the focusing state computation unit and configured to inspect the substrate supporting portion based on the focusing state determined by the focusing state computation unit.

14 Claims, 19 Drawing Sheets

(51) Int. Cl.
*G02B 26/08* (2006.01)
*G01N 21/956* (2006.01)
*G03F 7/20* (2006.01)
*H01L 21/66* (2006.01)
*G01N 21/94* (2006.01)

(52) U.S. Cl.
CPC ...... *G03F 7/70341* (2013.01); *G03F 7/70641* (2013.01); *G03F 7/70783* (2013.01); *H01L 22/12* (2013.01); *G01N 21/94* (2013.01); *G01N 2021/95615* (2013.01)

(56) References Cited

U.S. PATENT DOCUMENTS

| | | | |
|---|---|---|---|
| 8,115,916 | B2 | 2/2012 | Hayano |
| 8,256,370 | B2 | 9/2012 | Kitano et al. |
| 8,422,009 | B2 | 4/2013 | Yamashita et al. |
| 2004/0239918 | A1 | 12/2004 | Sugihara et al. |
| 2006/0232769 | A1 | 10/2006 | Sugihara et al. |
| 2008/0055575 | A1 | 3/2008 | Nagasaka et al. |
| 2009/0091752 | A1 | 4/2009 | Terasawa et al. |
| 2009/0123879 | A1 | 5/2009 | Hidaka |
| 2009/0285991 | A1 | 11/2009 | Kitano et al. |
| 2010/0103419 | A1 | 4/2010 | Sugihara et al. |
| 2010/0104173 | A1 | 4/2010 | Yoshida et al. |
| 2010/0271625 | A1 | 10/2010 | Matsui |
| 2011/0026017 | A1 | 2/2011 | Hayano |
| 2011/0096324 | A1 | 4/2011 | Watanabe et al. |
| 2011/0235038 | A1 | 9/2011 | Fukazawa et al. |
| 2013/0217154 | A1* | 8/2013 | Fukazawa ............ G03F 9/7026 438/7 |
| 2016/0379900 | A1* | 12/2016 | Maehr .................... H01L 22/26 438/7 |

FOREIGN PATENT DOCUMENTS

| | | |
|---|---|---|
| JP | 2006-80404 | 3/2006 |
| JP | 2006-105951 | 4/2006 |
| JP | 2007-304054 | 11/2007 |
| JP | 2009-277870 | 11/2009 |
| JP | 2010-153407 | 7/2010 |
| TW | 200823967 A | 6/2008 |
| TW | 200929335 A | 7/2009 |
| WO | WO 2009/091034 A1 | 7/2009 |
| WO | WO 2009/125805 A1 | 10/2009 |
| WO | WO 2010/052934 A1 | 5/2010 |

OTHER PUBLICATIONS

Chinese Office Action of Chinese Patent Application No. 201180059328.5 dated Feb. 28, 2015 (6 pages).
Taiwanese Office Action of Taiwan Application No. 100146165 dated Jan. 14, 2016 (15 pages).
Taiwanese Office Action of Taiwan Application No. 100146166 dated Jan. 11, 2016 (17 pages).
Notice of Reasons for Refusal issued in Japanese Patent Application No. 2012-548813, dated Aug. 18, 2015 (4 pages).
International Search Report, from the Japanese Patent Office for related PCT Application No. PCT/JP2011/078919, dated Jan. 17, 2012.
International Search Report, from the Japanese Patent Office of corresponding PCT Application No. PCT/JP2011/078819, dated Jan. 31, 2012.
Non-Final Office Action of U.S. Appl. No. 13/325,195, dated Aug. 14, 2014 (14 pages).
International Preliminary Report on Patentability of International Application No. PCT/JP2011/078819 dated Jun. 18, 2013 (6 pages).
International Preliminary Report of Patentability of International Application No. PCT/JP2011/078919 dated Jun. 18, 2013 (6 pages).
Notice of Allowance of U.S. Appl. No. 13/325,228, dated Oct. 3, 2014, (13 pages).
Ex Parte Quayle Action of U.S. Appl. No. 13/325,228 dated Jul. 22, 2014 (15 pages).
Notice of Reasons for Refusal issued in Japanese Patent Application No. 2012-548796, dated Nov. 17, 2015 (4 pages).

* cited by examiner

DEFOCUS PORTION

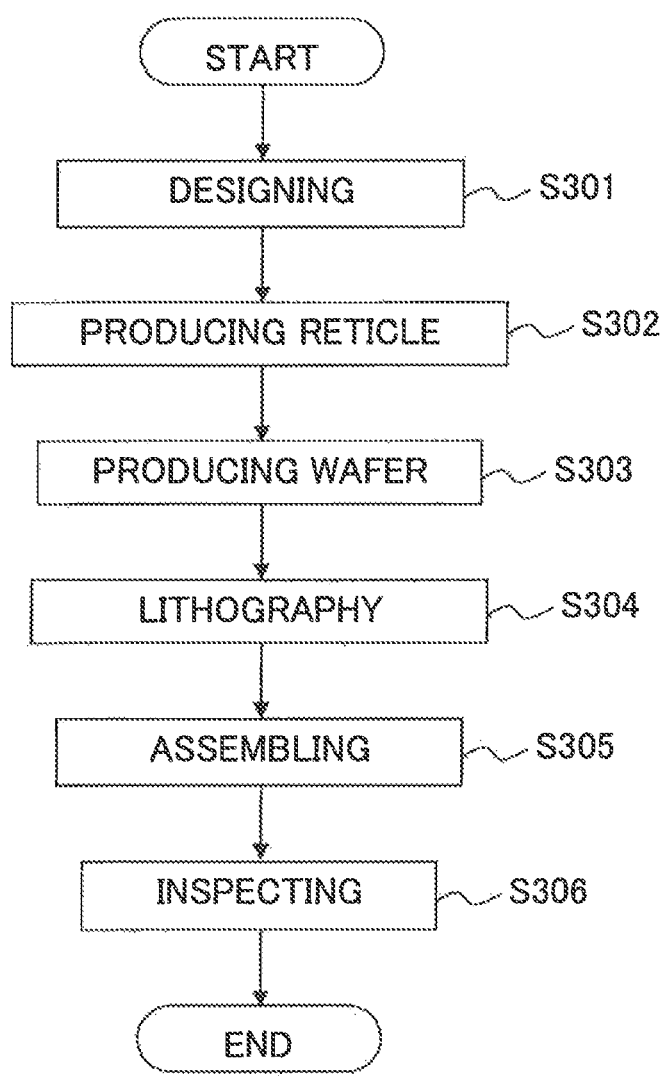

INSPECTION METHOD, INSPECTION APPARATUS, EXPOSURE CONTROL METHOD, EXPOSURE SYSTEM, AND SEMICONDUCTOR DEVICE

CROSS REFERENCE TO RELATED APPLICATIONS

The present application is a divisional application of U.S. patent application Ser. No. 13/325,228. The present application claims priority from Japanese Patent Application Nos. 2010-278308 and 2011-004306 filed respectively on Dec. 14, 2010 and on Jan. 12, 2011, all the disclosures of which are incorporated herein by reference in their entirety.

BACKGROUND

Field of the Invention

The present teaching relates to an inspection method for inspecting a substrate support portion configured to support substrates in exposure with an exposure device, an inspection apparatus, an exposure control method, and an exposure system. Further, the present teaching relates to a semiconductor device produced by utilizing such exposure system.

Description of the Related Art

In cases of producing semiconductor elements, liquid crystal elements and the like in a photolithography process, projection exposure devices are utilized to expose the pattern of a reticle (a photomask) to the semiconductor wafer on a stage (or a glass plate and the like) via a projection optical system. As an example of such projection exposure devices, exposure devices of step-and-scan type are known as carrying out exposure on one shot for a semiconductor wafer (to be referred to as a wafer hereinbelow) by relatively moving a reticle stage (i.e. a mask substrate with a mask pattern formed therein) to scan just one shot while irradiating with a slit-shaped light beam via a reticle pattern and a projection lens. In so doing, because the size of an exposure shot is determined by the relative distance of scanning between the long side of the slit (light) and the reticle stage, it is possible to enlarge the exposure shot.

In order for such kind of exposure device to hold the wafer motionlessly in a flat state, a wafer holder fixed on a wafer stage is to sucked the wafer and hold the same. When the exposure device continues the exposure, foreign substances come to adhere to the wafer holder such as resist residue and the like falling off the photoresist applied to the wafer. When the wafer is sucked and held on the wafer holder in this state, the foreign substances will deteriorate the flatness of wafer's exposure surface. This deterioration of flatness of the exposure surface becomes the cause of error of positional deviation and focus error in each shot region of the wafer, and turns out to be a major cause of deteriorating the yield rate in producing semiconductor elements. Therefore, exposure devices including a cleaning device are proposed for cleaning the wafer holder in such cases (for example, see Japanese Patent Application Laid-Open No. 2010-153407). According to this cleaning device, it is possible to clean the wafer supporting surface of the wafer holder by causing a cleaning member to contact with the wafer holder and moving the wafer holder via the wafer stage.

SUMMARY

According to an aspect of the present teaching, there is provided an inspection apparatus which inspects a substrate supporting portion configured to support a substrate during an exposure performed by an exposure apparatus, the apparatus including:

a irradiation unit which is configured to irradiate, with an illumination light beam, a surface of the substrate on which a pattern has been formed by an exposure by the exposure device;

a detecting unit which is configured to detect reflected light from a pattern in the irradiated surface;

a focusing state computation unit which is connected to the detection unit and which is configured to determine a focusing state of the pattern of the substrate, based on a detection result of the reflected light beam detected by the detection unit; and an inspection unit which is connected to the focusing state computation unit and which is configured to inspect the substrate supporting portion based on the focusing state determined by the focusing state computation unit.

BRIEF DESCRIPTION OF THE DRAWINGS

FIG. 20 is a flowchart showing a semiconductor device fabrication method.

DESCRIPTION OF THE EMBODIMENT

Figure 1:
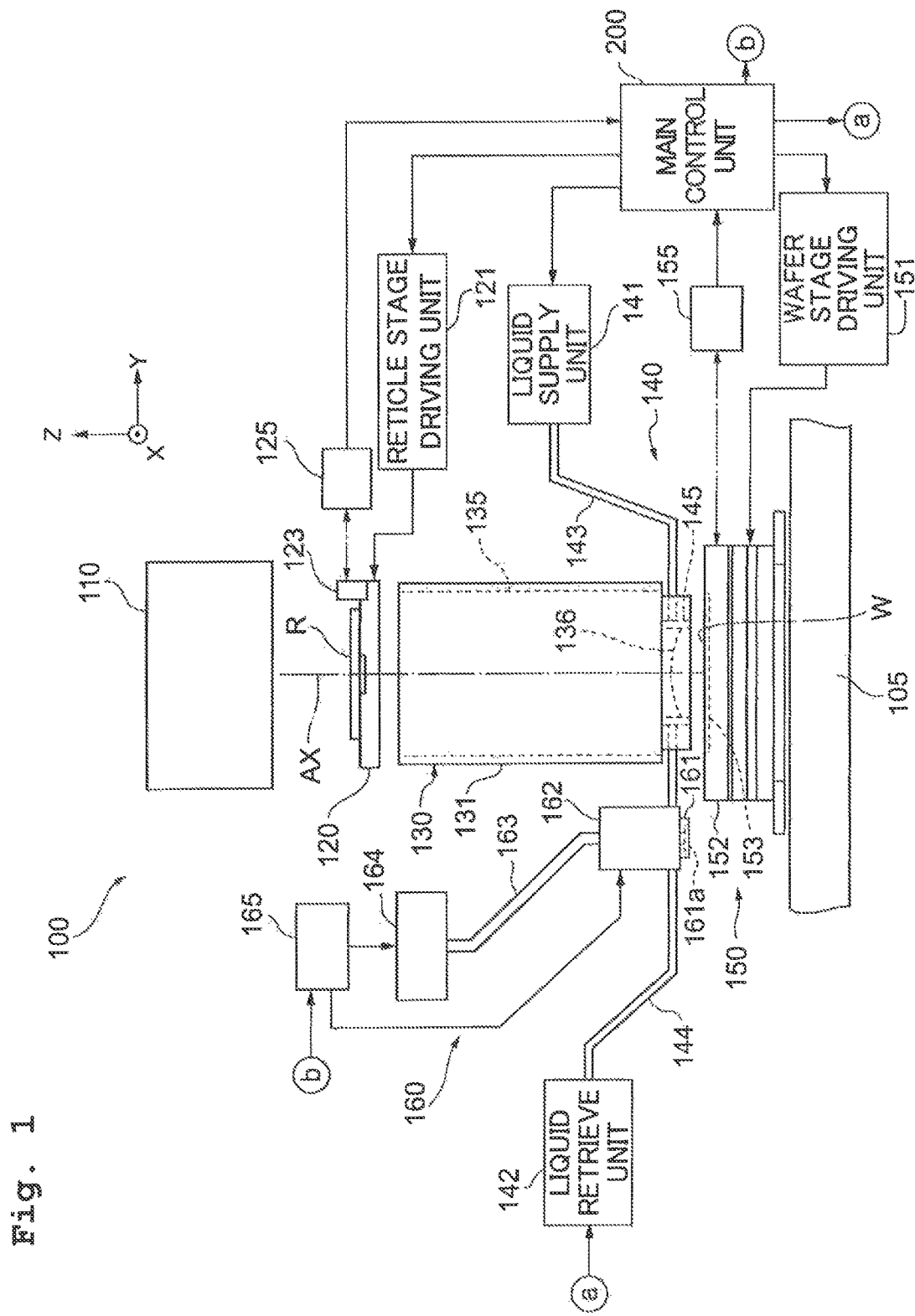
FIG. 1 shows an overall configuration of an exposure device.

Hereinbelow, referring to the accompanying drawings, an embodiment of the present teaching will be explained. An exposure stage inspection system in accordance with the embodiment includes an exposure device 100 configured to project and expose a predetermined mask pattern (repetitive pattern) onto the surface of a wafer to which resist is applied, and a surface inspection apparatus 1 configured to inspect the wafer with the repetitive pattern formed in the surface through an exposure process due to the exposure device 100, a development process due to a development device, and the like.

First, a configuration of the exposure device 100 will be explained with reference to FIG. 1. The exposure device 100 is configured to include an illumination system 110, a reticle stage 120, a projection unit 130, a local immersion device 140, a wafer stage 150, a cleaning device 160, and a main control device 200. Further, explanations will be made hereinbelow with the directions indicated by arrow marks X, Y and Z shown in FIG. 1 as the X-axis direction, Y-axis direction and Z-axis direction, respectively.

Detailed illustration being omitted, the illumination system 110 has a luminance uniformization optical system including a light source, an optical integrator and the like, and an illumination optical system including a reticle blind and the like, and is configured to illuminate a slit-shaped illumination region on a reticle R defined by the reticle blind with an illumination light beam (exposure light beam) of an approximately uniform luminance. As the illumination light, for example, ArF excimer laser light (wavelength 193 nm) is utilized.

On the reticle stage 120, the reticle R (photomask) is fixed and held by vacuum suction, for example, with a predetermined pattern (a line pattern, for example) formed in its pattern surface (the lower surface in FIG. 1). The reticle stage 120 is configured to be movable in the X-Y plane by a reticle stage drive device 121 including such as a linear motor, and movable at a predetermined scanning speed in the scanning direction (the Y-axis direction here).

A laser interferometer 125 detects positional information of the reticle stage 120 in the X-Y plane (including rotational information in the rotation direction about Z-axis) via a first reflector 123 having a reflection surface perpendicular to Y-axis and a second reflector (not shown) having a reflection surface perpendicular to X-axis, provided on the reticle stage 120. The positional information detected by the laser interferometer 125 is sent to the main control device 200, which controls the position (and the moving speed) of the reticle stage 120 via the reticle stage drive device 121 based on this positional information.

The projection unit 130 is configured to have a lens barrel 131 arranged below the reticle stage 120, and a projection optical system 135 held inside the lens barrel 131. The projection optical system 135 is configured to have a plurality of optical elements (lens elements) aligned along the optical axis AX of illumination light, and have a predetermined projection magnification (for example, ¼, ⅕, ⅛, or the like) on both telecentric sides. Therefore, when the illumination light beam emitted from the illumination system 110 illuminates the illumination region on the reticle R, by virtue of the illumination light beam transmitted through the reticle R arranged such that the objective surface of the projection optical system 135 is approximately consistent with the pattern surface, a diminished pattern image of the reticle R within the illumination region is formed in the exposure region on a semiconductor substrate wafer 10 (to be referred to as a wafer 10 hereinbelow) arranged on the imaging plane side of the projection optical system 135 (the region conjugative to the illumination region on the reticle R) via the projection optical system 135.

In the exposure device 100, the local immersion device 140 is provided to carry out exposure in an immersion method. The local immersion device 140 includes a liquid supply device 141, a liquid retrieve device 142, a liquid supply pipe 143, a liquid retrieve pipe 144, and a nozzle unit 145. The nozzle unit 145 is supported by a frame member (a member (not shown) constituting the exposure device 100) configured to support the projection unit 130 in such a manner as enclosing the periphery of the lower end of the lens barrel 131 holding the optical element closest to the imaging plane (the wafer side) constituting the projection optical system 135, i.e., the foremost lens 136 in the present case. In the embodiment, the nozzle unit 145 is set as shown in FIG. 1 such that its lower-end surface lies in almost the same plane with the lower-end surface of the foremost lens 136.

Detailed illustration being omitted, the liquid supply device 141 includes a tank storing liquid, a pressure pump, a temperature controller, and a valve configured to control liquid flow rate, and is connected to the nozzle unit 145 through the liquid supply pipe 143. Again detailed illustration being omitted, the liquid retrieve device 142 includes a tank storing retrieved liquid, a suction pump, and a valve configured to control liquid flow rate, and is connected to the nozzle unit 145 through the liquid retrieve pipe 144.

The main control device 200 controls the driving of the liquid supply device 141 and the liquid retrieve device 142. The main control device 200 controls the liquid supply device 141 to supply liquid (pure water, for example) to the portion between the foremost lens 136 and the wafer 10 through the liquid supply pipe 143, while controlling the liquid retrieve device 142 to retrieve the liquid from the portion between the foremost lens 136 and the wafer 10 through the liquid retrieve pipe 144. At this time, the main control device 200 controls the liquid supply device 141 and liquid retrieve device 142 such that the supplied liquid amount is constantly equal to the retrieved liquid amount. Therefore, between the foremost lens 136 and the wafer 10, a certain amount of liquid is constantly exchanged and maintained, whereby an immersion region (immersion space) is formed. In this manner, the exposure device 100 exposes the wafer 10 by irradiating the wafer 10 with the illumination light beam via the liquid forming the immersion region.

The wafer stage 150 is supported in a levitated manner by an air slide (not shown) above a base member 105 with a clearance of a few micrometers, and configured to be movable along the upper surface of the base member 105 within the X-Y plane by means of a wafer stage drive device 151 including a linear motor and the like.

A wafer table 152 is provided in the upper portion of the wafer stage 150, and a wafer holder 153 is fixed on the wafer table 152 to hold the wafer 10 by vacuum suction. Detailed illustration being omitted, in the upper surface of the wafer holder 153, i.e., the wafer supporting surface, a plurality of circular suction grooves are formed in connection with an external suction device including a vacuum pump and the like via a suction pipe. By applying a negative pressure to the space between the wafer supporting surface and the back side of the wafer 10 with this suction device, the wafer 10 is held on the wafer supporting surface of the wafer holder 153. Further, at the lateral side of the projection unit 130, an alignment device (not shown) is provided to detect the position of an alignment mark of the wafer 10 to be aligned by this alignment device.

Another laser interferometer 155 detects positional information of the wafer stage 150 in the X-Y plane via a reflection plane (a reflector) provided on the lateral side of the wafer table 152. The positional information detected by the laser interferometer 155 is sent to the main control device 200, which controls the position (and the moving speed) of the wafer stage 150 via the wafer stage drive device 151 based on this positional information.

In the exposure device 100 configured in the above manner, when the illumination light beam emitted from the illumination system 110 illuminates the illumination region on the reticle R, by virtue of the illumination light beam transmitted through the reticle R arranged such that the objective surface of the optical projection system 135 is approximately consistent with the pattern surface, a diminished pattern image of the reticle R within the illumination region is formed in the exposure region on the wafer 10 supported on the wafer stage 150 and arranged on the imaging plane side of the projection optical system 135 (the region conjugative to the illumination region on the reticle R) via the liquid of the immersion region formed by the projection optical system 135 and the local immersion device 140. Then, by synchronously driving the reticle stage 120 and the wafer stage 150, the reticle R is moved in the scanning direction with respect to the illumination region (the Y-axis direction), while the wafer 10 is also moved in the scanning direction with respect to the exposure region (the Y-axis direction). Accordingly, a scanning exposure is carried out in one shot region on the wafer 10, and thus the pattern image of the reticle R is transferred to that shot region.

When carrying out exposure on a number of wafers 10 in this manner, foreign substances such as resist residue and the like falling off the photoresist applied to the wafers 10 come to adhere to the wafer supporting surface of the wafer holder 153, and accumulates gradually to reach a large quantity at last. Thus, when the wafer holder 153 holds the wafer 10 on the foreign substances in this state, then the foreign substances deteriorate the flatness of exposure surface of the wafer 10 locally to become the cause of error of positional deviation and focus error in each shot region of the wafer. Therefore, the exposure device 100 is provided with the cleaning device 160 configured to eliminate the foreign substances on the wafer holder 153.

The cleaning device 160 includes a cleaning member 161 arranged at a lateral side of the projection unit 130 to face the wafer supporting surface of the wafer holder 153, a movement mechanism 162 configured to move the cleaning member 161 in X-axis, Y-axis and Z-axis directions respectively, a suction device 164 configured to carry out suction through a suction tube 163, and a cleaning control device 165 configured to control operation of the whole cleaning device 160. In the holder cleaning surface, which is the lower surface of the cleaning member 161, a suction port 161a is formed and connected through the suction tube 163 to the suction device 164 including a vacuum pump, foreign substance elimination filter and the like. The movement mechanism 162 is supported by a frame member (not shown) constituting the exposure device 100.

The cleaning control device 165 controls the driving of the movement mechanism 162 and the suction device 164. The cleaning control device 165 controls the operation of the movement mechanism 162 based on control information from the main control device 200 to cause the holder cleaning surface of the cleaning member 161 to contact with the wafer supporting surface of the wafer holder 153 positioned below the cleaning member 161 (to move the same in the Z-axis direction), while moving the cleaning member 161 relative to the wafer holder 153 in the X-Y plane. Further at this time, the cleaning control device 165 controls the operation of the suction device 164 to suck and eliminate the foreign substances on the wafer holder 153 by applying a negative pressure to the space in the vicinity of the suction port 161a of the cleaning member 161 via the suction tube 163.

In the exposure device 100 of such type, the operation of cleaning the wafer supporting surface of the wafer holder 153 is carried out by the cleaning device 160 based on the result of a surface inspection of the wafer 10. Here, the surface inspection of the wafer is performed after an exposure process is carried out by the exposure device 100, and after a development process due to a development device (not shown) and the like. Hereinbelow, explanations will be made with respect to the surface inspection apparatus 1 configured to carry out the surface inspection on the wafer 10.

Figure 2:
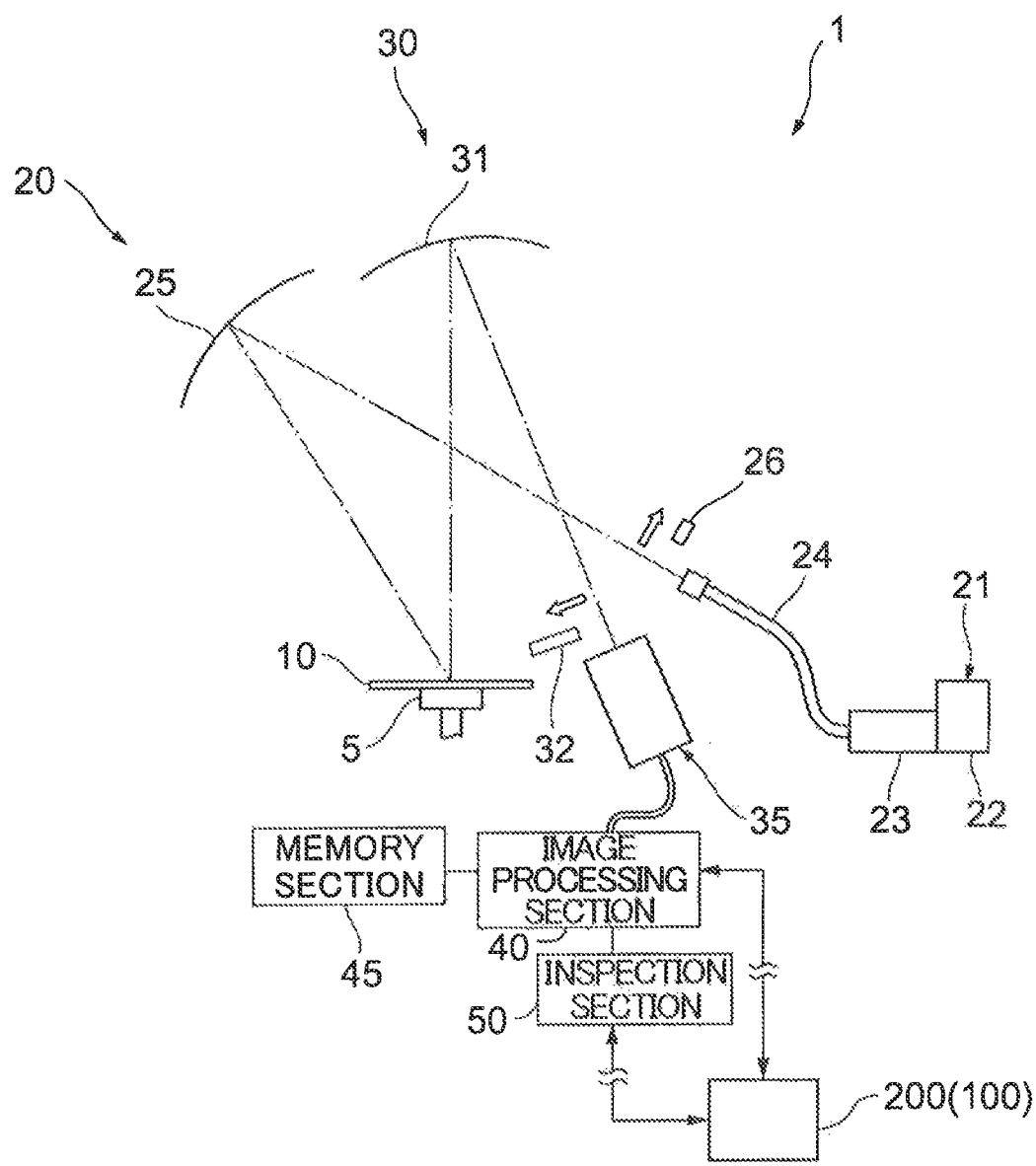
FIG. 2 shows an overall configuration of a surface inspection apparatus.

As shown in FIG. 2, the surface inspection apparatus 1 includes an inspection stage 5 configured to support the approximately disk-shaped wafer 10, which is carried therein by a carrier device (not shown) and placed on the inspection stage 5 while being fixed and held by vacuum suction. The inspection stage 5 supports the wafer 10 to be rotatable (within the surface of the wafer 10) with a rotational symmetrical axis of the wafer 10 (the central axis of the inspection stage 5) as the rotation axis. Further, the inspection stage 5 is configured to be able to tilt the wafer 10 about an axis through the surface of the wafer 10, and to be able to adjust the incidence angle of illumination light.

Further, the surface inspection apparatus 1 includes an illumination system 20 configured to irradiate the surface of the wafer 10 supported on the inspection stage 5 with an illumination light beam as a parallel light beam, a light receiving system 30 configured to condense reflected light, diffracted light and the like from the wafer 10 receiving the irradiation of the illumination light beam, an imaging device 35 configured to capture an image of the surface of the wafer 10 receiving the light beam condensed by the light receiving system 30, an image processing section 40, and an inspection section 50. The illumination system 20 includes an illumination unit 21 configured to emit the illumination light beam, and an illumination-side concave mirror 25 configured to reflect the illumination light beam emitted from the illumination unit 21 toward the surface of the wafer 10. The illumination unit 21 includes a light source 22 such as a metal halide lamp, a mercury lamp and the like, a light adjusting section 23 (a dimmer 23) configured to adjust light intensity by extracting the light beam having a predetermined wavelength from the light from the light source 22, and a light guiding fiber 24 configured to guide the light beam from the light adjusting section 23 as the illumination light beam to the illumination-side concave mirror 25.

Then, the light beam from the light source 22 is transmitted through the light adjusting section 23, and the illumination light beam having a predetermined wavelength (248 nm, for example) is emitted from the light guiding fiber 24 to the illumination-side concave mirror 25. Then, because the exit portion of the light guiding fiber 24 is arranged on the focal plane of the illumination-side concave mirror 25, the illumination light beam emitted from the light guiding fiber 24 to the illumination-side concave mirror 25 becomes a parallel light beam due to the illumination-side concave mirror 25 to irradiate the surface of the wafer 10 held on the inspection stage 5. Further, it is possible to adjust the relation between the incoming angle and the outgoing angle to the wafer 10 for the illumination light by tilting the inspection stage 5 to change the angle of placing the wafer 10.

Figure 3:
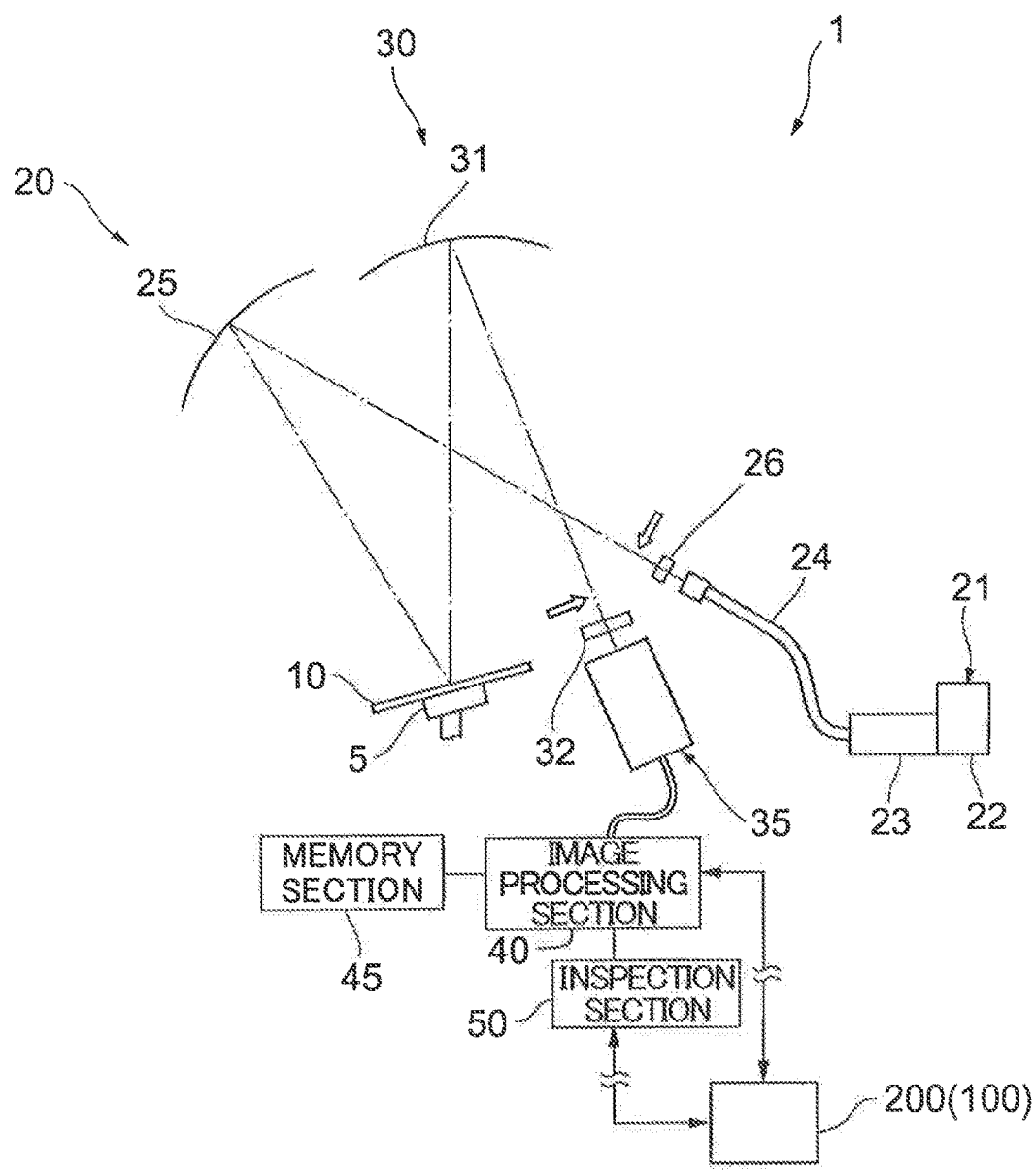
FIG. 3 shows a state of inserting a polarizing filter into an optical path of the surface inspection apparatus.

Further, an illumination-side polarizing filter 26 is provided to be insertable into and removable from the optical path between the light guiding fiber 24 and the illumination-side concave mirror 25. As shown in FIG. 2, with the illumination-side polarizing filter 26 removed from the optical path, inspection is carried out by utilizing diffracted light (to be referred to as diffraction inspection hereinbelow for convenience) and, as shown in FIG. 3, with the illumination-side polarizing filter 26 inserted in the optical path, inspection is carried out by utilizing polarized light (change in polarization state due to structural birefringence). This inspection will be referred to as PER inspection hereinbelow for convenience, and the illumination-side polarizing filter 26 will be described in detail hereinafter.

The light receiving system 30 condenses the exit light beam (diffracted or reflected light beam) from the surface of the wafer 10. The light receiving system 30 mainly includes a light-receiving-side concave mirror 31 provided to face the inspection stage 5. The exit light beam condensed by the light-receiving-side concave mirror 31 (diffracted or reflected light beam) reaches the imaging plane of the imaging device 35 to form an image of the wafer 10.

Further, a light-receiving-side polarizing filter 32 is provided to be insertable into and removable from the optical path between the light-receiving-side concave mirror 31 and the imaging device 35. As shown in FIG. 2, with the light-receiving-side polarizing filter 32 removed from the optical path, diffraction inspection is carried out. As shown in FIG. 3, with the light-receiving-side polarizing filter 32 inserted in the optical path, PER inspection is carried out (the light-receiving-side polarizing filter 32 will be described in detail hereinafter).

The imaging device 35 photoelectrical converts the surface image of the wafer 10 formed on the imaging plane to generate an image signal and output the image signal to the image processing section 40. The image processing section 40 generates a digital image of the wafer 10 based on the image signal of the wafer 10 inputted from the imaging device 35. An inner memory (not shown) of the image processing section 40 previously stores image data of nondefective wafers. After generating an image of the wafer 10 (digital image), the image processing section 40 compares the image data of the wafer 10 with the image data of nondefective wafers, and the inspection section 50 inspects whether or not there is any defect (abnormity) in the surface of the wafer 10. Then, the inspection result from the image processing section 40 and inspection section 50, and the image of the relevant wafer 10 are outputted and displayed on an image display device (not shown). Further, the image processing section 40 is configured to be capable of finding a focus variation state of the exposure device 100 by utilizing the wafer image (details will be described hereinafter).

Figure 4:
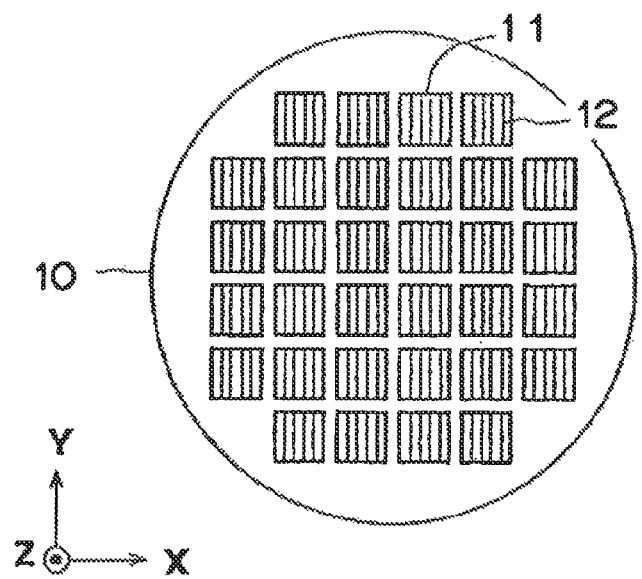
FIG. 4 is an external plan view of a surface of a semiconductor wafer.

However, the exposure device 100 projects a predetermined mask pattern on the wafer 10 and exposes the uppermost resist film of the wafer 10. The wafer 10 is developed by a development device (not shown) and then carried onto the inspection stage 5 by a carrier device (not shown) from a wafer cassette (not shown) or the development device. At this time, the wafer 10 is carried onto the inspection stage 5 in a state of being aligned with the pattern or the outer edge (notch, orientation flat or the like) of the wafer 10 as the reference. Further, on the surface of the wafer 10, as shown in FIG. 4, a plurality of chip regions 11 (shots) are arranged horizontally and vertically (in X- and Y-directions in FIG. 4), and in each chip region 11, a repetitive pattern 12 is formed as a semiconductor pattern such as a line pattern, a hole pattern, or the like. Further, the exposure device 100 is an exposure device of the aforementioned step-and-scan type, is electrically connected to a signal output portion (not shown) of the surface inspection apparatus 1 of the embodiment via cables and the like, and is configured to be capable of exposure control adjustment based on the data (signal) from the surface inspection apparatus 1.

In order to utilize the surface inspection apparatus 1 configured in the above manner to carry out diffraction inspection of the surface of the wafer 10, first, the illumination-side polarizing filter 26 and the light-receiving-side polarizing filter 32 are removed from the optical path as shown in FIG. 2, and the wafer 10 is carried onto the inspection stage 5 by the carrier device (not shown). It is possible to place the wafer 10 on the inspection stage 5 in predetermined position and direction by an alignment mechanism (not shown) since the alignment mechanism acquires positional information of the pattern formed in the surface of the wafer 10 during the period of carrying.

Next, the inspection stage 5 is rotated such that the direction of illuminating the surface of the wafer 10 is consistent with the repetitive direction of the pattern (in the case of a line pattern, perpendicular to the line) and, meanwhile, set to satisfy the following equation (1) by Huygens' principle (to tilt the inspection stage 5), where P represents the pattern pitch, $\lambda$ represents the wavelength of the illumination light beam irradiating the surface of the wafer 10, $\theta 1$ represents the incidence angle of the illumination light beam, and $\theta 2$ represents the exit angle of the nth-order diffracted light beam.

$$P = n \times \lambda / \{\sin(\theta 1) - \sin(\theta 2)\} \quad \text{(Eq. 1)}$$

Next, the illumination system 20 irradiates the surface of the wafer 10 with the illumination light beam. When irradiating the surface of the wafer 10 with the illumination light beam under such a condition, the light beam from the light source 22 in the illumination unit 21 is transmitted through the light adjusting section 23. The illumination light beam having a predetermined wavelength (248 nm, for example) exits from the light guiding fiber 24 to the illumination-side concave mirror 25, and the illumination light beam reflected by the illumination-side concave mirror 25 becomes a parallel light beam to irradiate the surface of the wafer 10. The diffracted light beam diffracted by the surface of the wafer 10 is condensed by the light-receiving-side concave mirror 31, and reaches the imaging plane of the imaging device 35 to form an image (due to diffracted light) of the wafer 10.

Here, the imaging device 35 photoelectrical converts the surface image of the wafer 10 formed on the imaging plane to generate an image signal, and outputs the image signal to the image processing section 40. The image processing section 40 generates a digital image of the wafer 10 based on the image signal of the wafer 10 inputted from the imaging device 35 (the digital image of the wafer 10 based on diffracted light will be referred to as a diffraction image hereinbelow for convenience). Further, after generating a diffraction image of the wafer 10, the image processing section 40 compares the image data of the wafer 10 with the image data of nondefective wafers and sends the comparison result to the inspection section 50. The inspection section 50 inspects whether or not there is any defect (abnormity) in the surface of the wafer 10, and inspects the focusing state (the focusing state in exposing the pattern). Then, the inspection result from the image processing section 40 and inspection section 50, and the diffraction image of the relevant wafer 10 are outputted and displayed on the image display device (not shown). Further, when easy to be affected by lower layers, it is possible to reduce the affect from lower layers by arranging the illumination-side polarizing filter 26 in the illumination system 20 such that the illumination light becomes an S-polarized light, and illuminating with the S-polarized light. Further, in this case, the light-receiving-side polarizing filter 32 should also be removed from the optical path.

Figure 5:
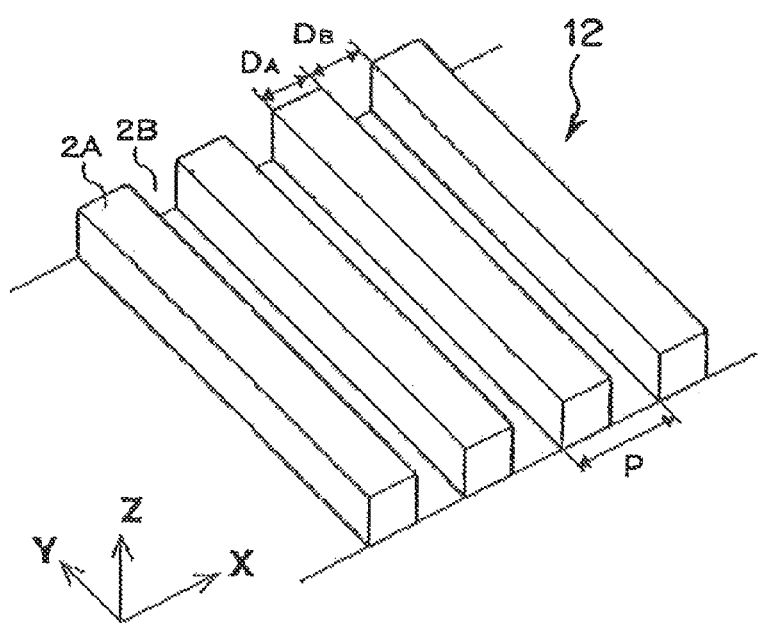
FIG. 5 is a perspective view for explaining a concavo-convex structure of a repetitive pattern.

Next, explanations will be made with respect to the case of carrying out PER inspection of the surface of the wafer 10 by the surface inspection apparatus 1. Further, the repetitive pattern 12 is supposed to be, as shown in FIG. 5, a resist pattern (line pattern) where a plurality of line portions 2A are aligned with a certain pitch P along the short side direction (X-direction). Further, there is a space portion 2B between adjacent line portions 2A. Further, the direction of aligning the line portions 2A (X-direction) will be referred to as the "repetitive direction of the repetitive pattern 12".

Here, the design value of line width $D_A$ of the line portions 2A in the repetitive pattern 12 is supposed to be ½ of the pitch P. When the repetitive pattern 12 is formed just as following the design value, then the line width $D_A$ of the line portions 2A is equal to the line width $D_B$ of the space portions 2B, and the volume ratio between the line portion 2A and the space portion 2B is approximately 1:1. On the other hand, when the exposure focus deviates from a correct value in forming the repetitive pattern 12, then the pitch P does not change but the line width $D_A$ of the line portions 2A differs from the design value and from the line width $D_B$ of the space portions 2B and, as a result, the volume ratio between the line portion 2A and the space portion 2B deviates from 1:1.

The PER inspection utilizes the change in the volume ratio between the line portion 2A and the space portion 2B in the repetitive pattern 12 as described above to carry out abnormity inspection of the repetitive pattern 12. Further, in order to simplify explanations, the ideal volume ratio (design value) is supposed to be 1:1. The change in volume ratio is because the exposure focus deviates from the correct value, and appears in each shot region of the wafer 10. Further, it is possible to rephrase the volume ratio as the area ratio of cross-section shape.

Figure 6:
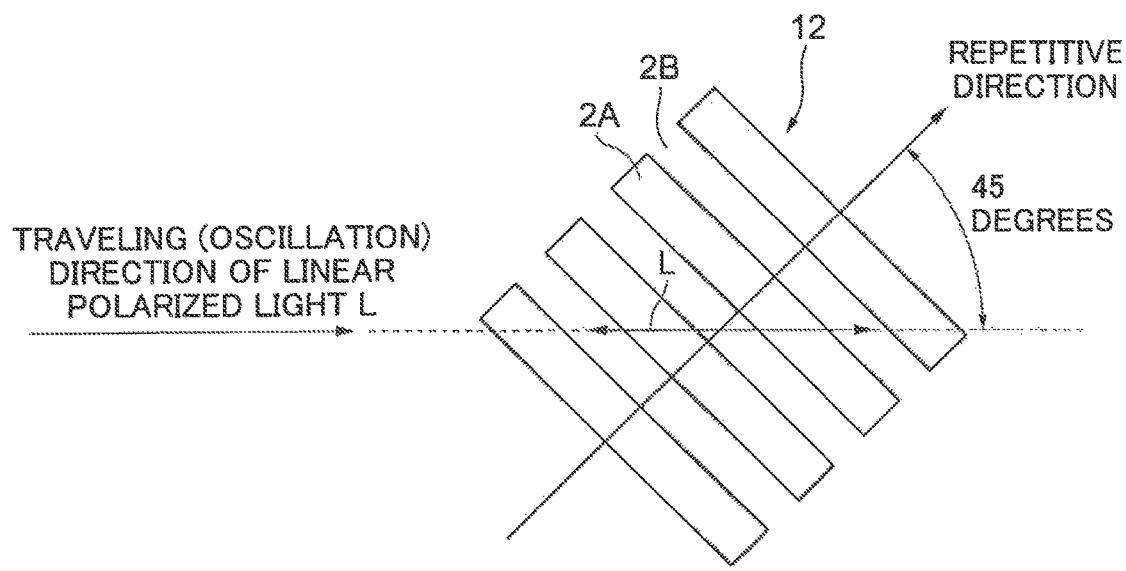
FIG. 6 is a diagram for explaining a state of inclination between the incidence surface of a linear polarized light and the repetitive direction of the repetitive pattern.

In the PER inspection, as shown in FIG. 3, the illumination-side polarizing filter 26 and the light-receiving-side polarizing filter 32 are inserted into the optical path. Further, when carrying out the PER inspection, the inspection stage 5 tilts the wafer 10 at an inclination angle such that the light receiving system 30 can receive the specular light from the wafer 10 irradiated by the illumination light, while stopping at a predetermined rotation position, and maintaining the repetitive direction of the repetitive pattern 12 in the wafer 10 as about 45 degrees oblique to the oscillation direction of the illumination light (linear polarized light L) on the surface of the wafer 10 as shown in FIG. 6. According to the knowledge of the present inventors, when the angle between the repetitive direction of the repetitive pattern 12 in the wafer 10 and the oscillation direction of the illumination light is set to be about 45 degrees, it is possible to maximize the amount of light for inspecting the repetitive pattern 12. Further, according to the knowledge of the present inventors, when the angle between the repetitive direction of the repetitive pattern 12 in the wafer 10 and the oscillation direction of the illumination light is set to be about 22.5 degrees or about 67.5 degrees, it is possible to enhance the sensitivity of inspection. It goes without saying that the angle is not limited to these degrees but may be set in arbitrary angular directions.

The illumination-side polarizing filter 26 is provided between the light guiding fiber 24 and the illumination-side concave mirror 25, and the transmission axis of the illumination-side polarizing filter 26 is set in a predetermined azimuth direction to extract the linear polarized light from the light beam from the illumination unit 21 according to the transmission axis. At this time, because the exit portion of the light guiding fiber 24 is arranged in the focal position of the illumination-side concave mirror 25, the illumination-side concave mirror 25 makes the light transmitted through the illumination-side polarizing filter 26 be a parallel light beam to irradiate the substrate wafer 10. In this manner, the light beam exiting the light guiding fiber 24 becomes the linear polarized light L of P-polarization (see FIG. 6) via the illumination-side polarizing filter 26 and the illumination-side concave mirror 25 to irradiate the entire surface of the wafer 10 as an illumination light.

At this time, because the proceeding direction of the linear polarized light L (the direction of the main light beam of the linear polarized light L reaching any points on the surface of the wafer 10) is approximately parallel to the optical axis, the incidence angle of the linear polarized light L at each point of the wafer 10 is identical to each other due to the parallelity. Further, because the linear polarized light L incident on the wafer 10 is p-polarized, as shown in FIG. 6, when the repetitive direction of the repetitive pattern 12 is set at a 45-degree angle to the incidence surface of the linear polarized light L (the proceeding direction of the linear polarized light L on the surface of the wafer 10), the angle formed between the oscillation direction of the linear polarized light L on the surface of the wafer 10 and the repetitive direction of the repetitive pattern 12 is also set at 45 degrees. In other words, the linear polarized light L enters the repetitive pattern 12 such that the oscillation direction of the linear polarized light L on the surface of the wafer 10 is inclined 45 degrees with respect to the repetitive direction of the repetitive pattern 12 and that the linear polarized light L obliquely traverses the repetitive pattern 12.

The specular light beam reflected by the surface of the wafer 10 is condensed by the light-receiving-side concave mirror 31 of the light receiving system 30 and reaches the imaging plane of the imaging device 35. At this time, the polarization state of the linear polarized light L changes due to the form birefringence in the repetitive pattern 12. The light-receiving-side polarizing filter 32 is provided between the light-receiving-side concave mirror 31 and the imaging device 35, and the azimuth of the transmission axis of the light-receiving-side polarizing filter 32 is set to be perpendicular to the transmission axis of the illumination-side polarizing filter 26 described above (a crossed Nichol state). Therefore, the light-receiving-side polarizing filter 32 can transmit the polarized component (the s-polarized component, for example) almost orthogonal in oscillation direction to the linear polarized light L in the specular light from the wafer 10 (the repetitive pattern 12) to lead the same to the imaging device 35. As a result, on the imaging plane of the imaging device 35, a reflection image of the wafer 10 is formed by the polarized component almost orthogonal in oscillation direction to the linear polarized light L among the specular light beams from the wafer 10. Further, it is possible to improve the sensitivity by making the light-receiving-side polarizing filter 32 be rotatable about the optical axis and adjust the same such that the minor axis of the elliptically polarized specular light coincides with the transmission axis of the light-receiving-side polarizing filter 32. In this case, the adjusting angle is a few degrees. Therefore, it is possible to say that the azimuth of the transmission axis of the light-receiving-side polarizing filter 32 is set to be substantially perpendicular to the transmission axis of the illumination-side polarizing filter 26.

In order for the surface inspection apparatus 1 to carry out the PER inspection of the surface of the wafer 10, first, as shown in FIG. 3, the illumination-side polarizing filter 26 and the light-receiving-side polarizing filter 32 are inserted into the optical path, and the wafer 10 is carried onto the stage 5 by the carrier device (not shown). Further, it is possible to place the wafer 10 on the stage 5 in predetermined position and direction since the alignment mechanism (not shown) acquires positional information of the pattern formed in the surface of the wafer 10 in carrying. Further, at this time, the stage 5 tilts the wafer 10 at an inclination angle such that the light receiving system 30 can receive the specular light from the wafer 10 irradiated by the illumination light. Further, the stage 5 stops at a predetermined rotation position to maintain the repetitive direction of the repetitive pattern 12 in the wafer 10 as 45 degrees oblique to the oscillation direction of the illumination light (linear polarized light L) on the surface of the wafer 10.

Next, the illumination system 20 irradiates the surface of the wafer 10 with the illumination light beam. When irradiating the surface of the wafer 10 with the illumination light beam under such a condition, the light beam exiting from the light guiding fiber 24 of the illumination unit 21 becomes the linear polarized light L of P-polarization via the illumination-side polarizing filter 26 and the illumination-side concave mirror 25 to irradiate the entire surface of the wafer 10 as an illumination light. The specular light beam reflected by the surface of the wafer 10 is condensed by the light-receiving-side concave mirror 31, and reaches the imaging plane of the imaging device 35 to form a (reflection) image of the wafer 10.

At this time, the polarization state of the linear polarized light L changes due to the form birefringence in the repetitive pattern 12. The light-receiving-side polarizing filter 32 can transmit the polarized component almost orthogonal in oscillation direction to the linear polarized light L in the specular light from the wafer 10 (the repetitive pattern 12), i.e., extract the change in the polarization state of the linear polarized light L, to lead the same to the imaging device 35. As a result, a reflection image of the wafer 10 is formed on the imaging plane of the imaging device 35, by the polarized component almost orthogonal in oscillation direction to the linear polarized light L among the specular light beams from the wafer 10.

Here, the imaging device 35 photoelectrical converts the surface image (reflection image) of the wafer 10 formed on the imaging plane to generate an image signal (digital image data), and outputs the image signal to the image processing section 40 via the main control section 50. The image processing section 40 generates a digital image of the wafer 10 based on the image signal of the wafer 10 inputted from the imaging device 35 (the digital image of the wafer 10 based on polarized light beam will be referred to as the polarization image hereinbelow for convenience). Further, the image processing section 40 sends the polarization image to the inspection section 42 via the main control section 50 after generating the polarization image of the wafer 10, and the inspection section 42 compares the image data of the wafer 10 with the image data of nondefective wafers to inspect whether or not there is any defect (abnormity) in the surface of the wafer 10. Further, since the signal intensity (brightness value) of the reflection image of nondefective wafers is conceivably to show the maximum signal intensity (brightness value), for example, "abnormity" is determined when the change in signal intensity (brightness) compared with nondefective wafers is greater than a predetermined threshold value (allowable value), while "normality" is determined when it is less than the threshold value. Then, the inspection result from the image processing section 40 and the inspection section 42, and the polarization image of the relevant wafer 10 are outputted and displayed on the image display device (not shown).

Further, the signal intensity refers to that according to the light detected by the imaging element of the imaging device 35 such as diffraction efficiency, intensity ratio, energy ratio, and the like. The present teaching is not limited to the above diffraction inspection and PER inspection, it is also possible to carryout inspection based on the specular light from the surface of the wafer 10 (to be referred to as the specular inspection hereinbelow for convenience). When carrying out the specular inspection, the image processing section 40 generates a digital image based on the specular light from the surface of the wafer 10 (to be referred to as the specular image hereinbelow for convenience) to inspect whether or not there is any defect (abnormity) in the surface of the wafer 10 based on the generated specular image of the wafer 10.

Further, the inspection section 42 can find a focus curve due to the diffracted light of the exposure device 101 (a curve showing a relationship between the focus offset and the signal intensity) by utilizing an image of a developed wafer exposed under the condition of changing the focus offset of the exposure device 101 for each shot. Utilizing this focus curve to find the focus offset for the signal intensity of diffracted light to become maximal for each minute region in one shot, it is possible to find inclination of the image plane of the mask pattern projected and exposed by the exposure device 101. According to the knowledge of the present inventors, in the case of diffracted light, when the line-and-space duty ratio is set to be not less than ten (one line unit to ten or more space units), then the focus offset in which the signal intensity becomes maximal is the best focus.

Figure 7:
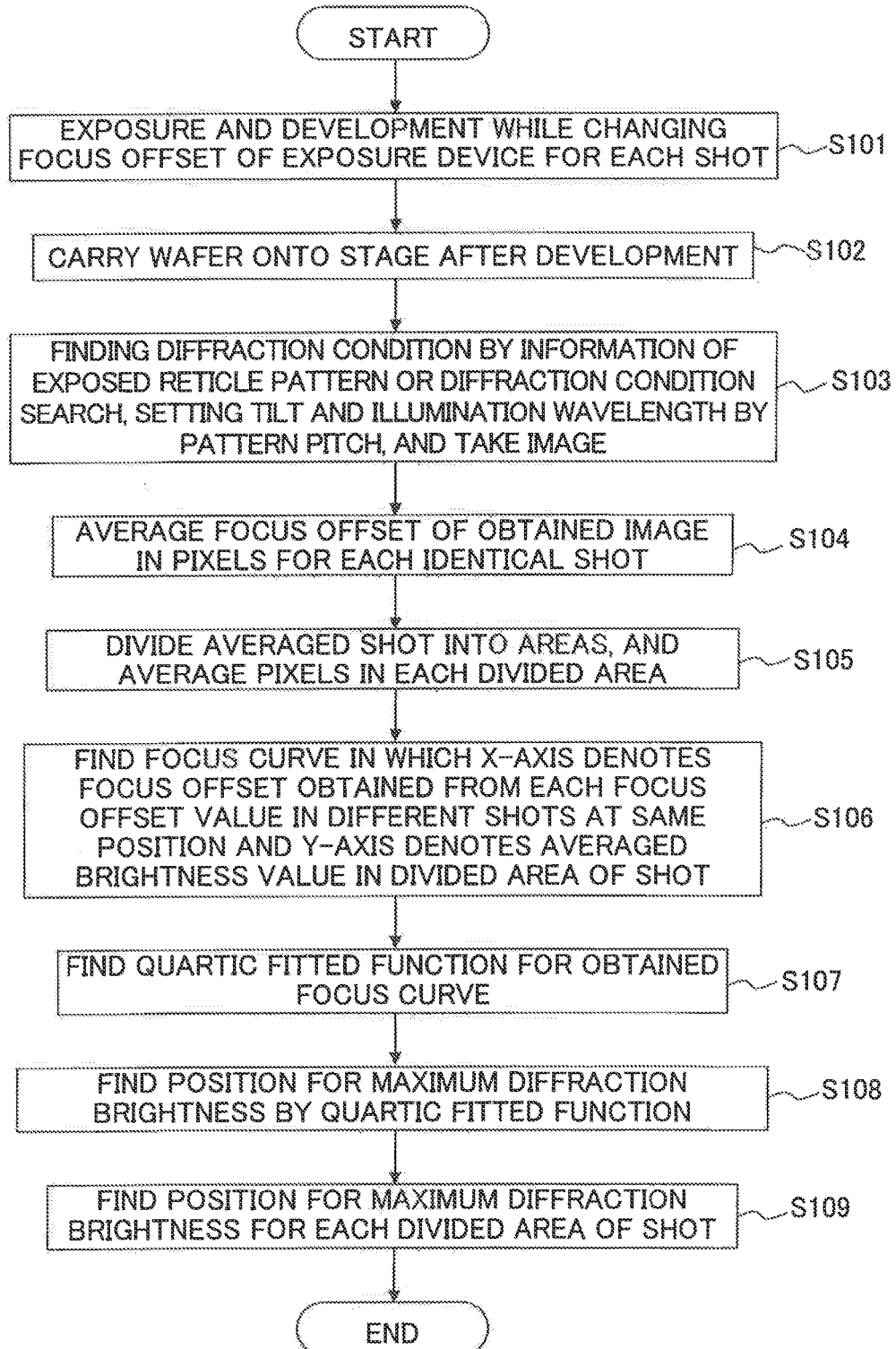
FIG. 7 is a flowchart showing a method for finding inclination of the image plane of the exposure device.

Hereinbelow, referring to the flowchart shown in FIG. 7, explanations will be made with respect to a method for finding the inclination of the image surface of the mask pattern projected and exposed by the exposure device 100. First, a wafer is produced with a repetitive pattern formed by changing the focus offset (predetermined) of the exposure device 100 (step S101). At this time, the process of exposure and development is carried out by changing the focus offset for each exposure shot, setting a plurality of shots with the same focus offset, and arranging the plurality of shots discretely (at random positions). Hereinbelow, such kind of wafer will be referred to as a condition-parameterizing wafer 10*a* (see FIGS. 8 and 9).

Here, the purpose of changing the focus offset into a matrix form is to cancel out, for example, the difference in the resist condition occurring between the central side and the circumferential side of a wafer, and the influence of a so-called left-right difference and the like in scanning exposure. Further, since the resist film (photoresist) on the wafer is often formed by application of spin coat. As the resist solution spreads due to the spin, the solvent component vaporizes accordingly, and thereby the viscosity increases. For this reason, the film tends to become thicker to give rise to the difference in the resist condition between the central side and the circumferential side of the wafer. The so-called left-right difference is, for example, the difference in exposure while the reticle is moving in the positive X-direction (the wafer is moving in the negative X-direction), or the difference in exposure while the reticle is moving in the negative X-direction (the wafer is moving in the positive X-direction), when the scanning direction is taken as the X-direction.

Figure 8:
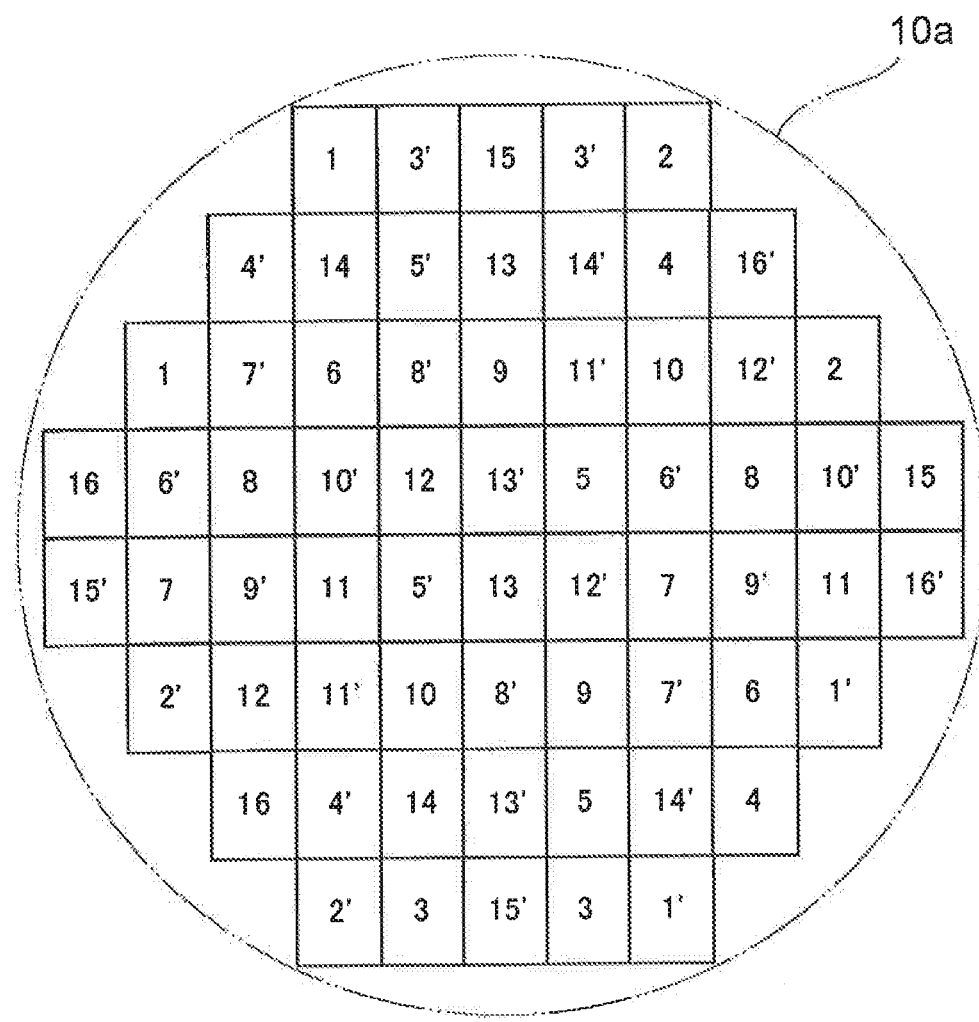
FIG. 8 shows a focus offset set by a condition-parameterizing wafer.

The condition-parameterizing wafer 10a gradates the focus offset into 16 steps by 25 nm from −175 nm to +200 nm as shown in FIG. 8, for example. Further, in each shot of FIG. 8, the number (1 to 16) denotes the step of the focus offset gradated by 25 nm, where """ is assigned to the case with the same step but opposite scanning direction. For example, like the shot of the focus offset denoted by the number 12, it is possible to set an exposure to be carried out with the same focus offset in four places such as one shot at positive X-direction reticle movement/central side; one shot at positive X-direction reticle movement/circumferential side; one shot at negative X-direction reticle movement/ central side; and one shot at negative X-direction reticle movement/circumferential side. Further for example, like the shot of the focus offset denoted by the number 15, it is possible to set an exposure to be carried out with the same focus offset with the center of the condition-parameterizing wafer 10a as the symmetrical axis in four places such as two shots at positive X-direction reticle movement/circumferential side; and two shots at negative X-direction reticle movement/circumferential side. In the example of FIG. 8, the condition-parameterizing wafer 10a is produced with totally 64 shots by four shots of each focus offset in 16 steps of the focus offset in the above manner by discretely arranging those shots.

Further, a plurality of condition-parameterizing wafers may as well be produced to find the focus curve. In this case, it is possible to set the shot arrangement according to each focus offset of each condition-parameterizing wafer to cancel out the influence due to other conditions than focus offset.

After producing the condition-parameterizing wafer 10a, in the same manner as in the case of diffraction inspection, the condition-parameterizing wafer 10a is carried onto the inspection stage 5 (step S102). Next, still in the same manner as in the case of diffraction inspection, the illumination system 20 irradiates the surface of the condition-parameterizing wafer 10a with the illumination light beam, the imaging device 35 photoelectrically converts the diffraction image of the condition-parameterizing wafer 10a to generate an image signal and output the image signal to the image processing section 40 (step S103). At this time, the condition-parameterizing wafer 10a is set in the same manner as in the case of the diffraction inspection to find the diffraction condition by utilizing information of the exposed mask pattern or diffraction condition search (to measure the intensity of the diffracted light by tilting the inspection stage 5 in a angular range other than specular condition), and obtain the diffracted light.

Figure 9:
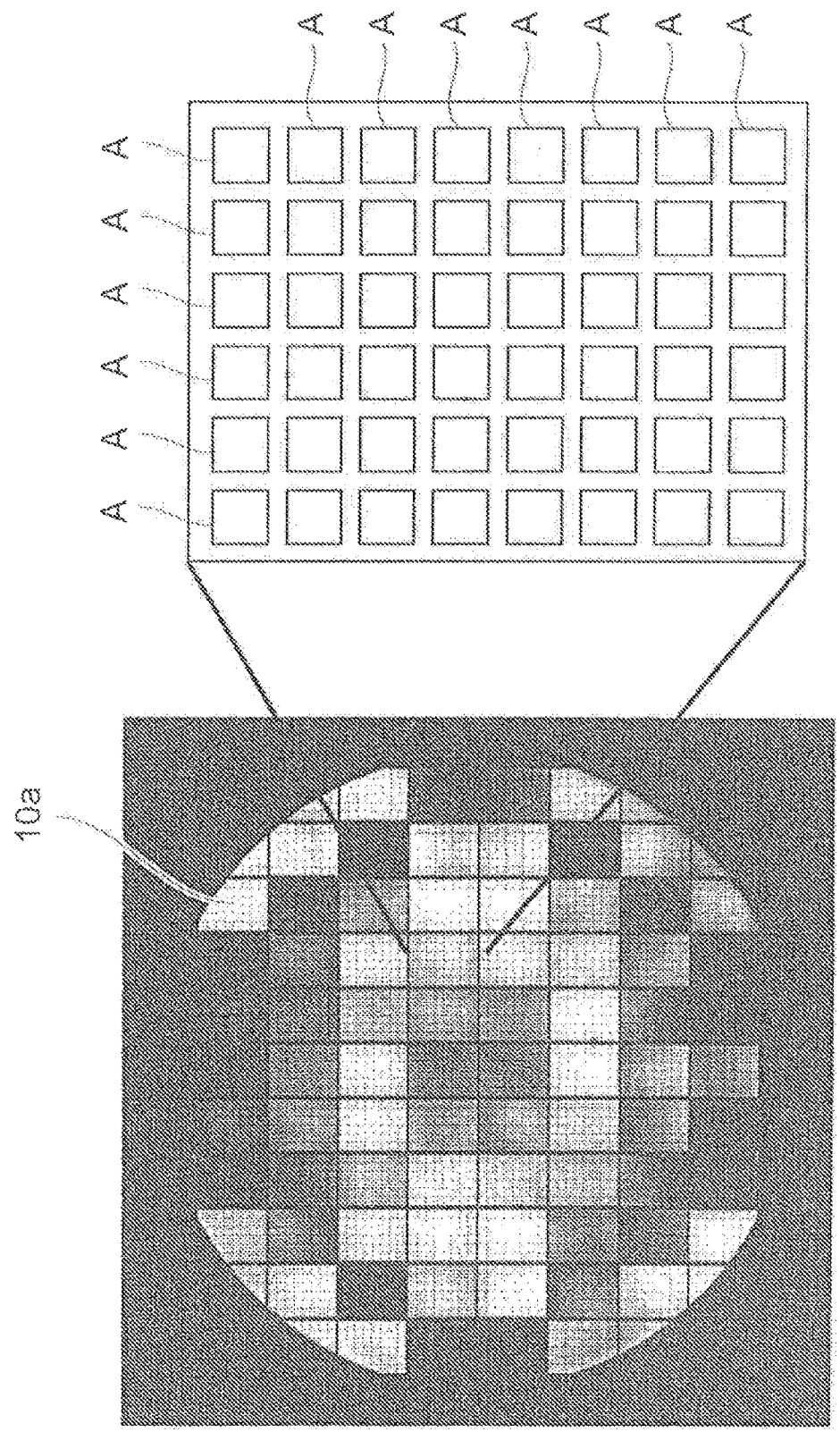
FIG. 9 shows an example of the condition-parameterizing wafer.

Next, based on the image signal of the condition-parameterizing wafer 10a inputted from the imaging device 35, the image processing section 40 generates a diffraction image of the condition-parameterizing wafer 10a, and carries out averaging of the signal intensity in the unit of pixels (the pixel group of the portion corresponding to each shot) for each shot of the same focus offset (step S104). Further, the portion determined to be defective in the diffraction inspection is excluded from the object of the above averaging. Next, with respect to all the shots obtained by the averaging, i.e., the shots different in focus offset from each other, the image processing section 40 finds the average value of the signal intensity (to be referred to as the average brightness hereinbelow for convenience), respectively, in a plurality of setting areas A (the areas encircled by a small rectangle) set in the shot as shown in FIG. 9 (step S105). Further, because the focus offset of the exposure device 100 is changed for each shot in the condition-parameterizing wafer 10a, it is possible to find the focus offset from the shot position. Thereby, in the setting area A of the same position in each shot exposed the different focus offset, the average brightness changes according to the focus offset.

Figure 10:
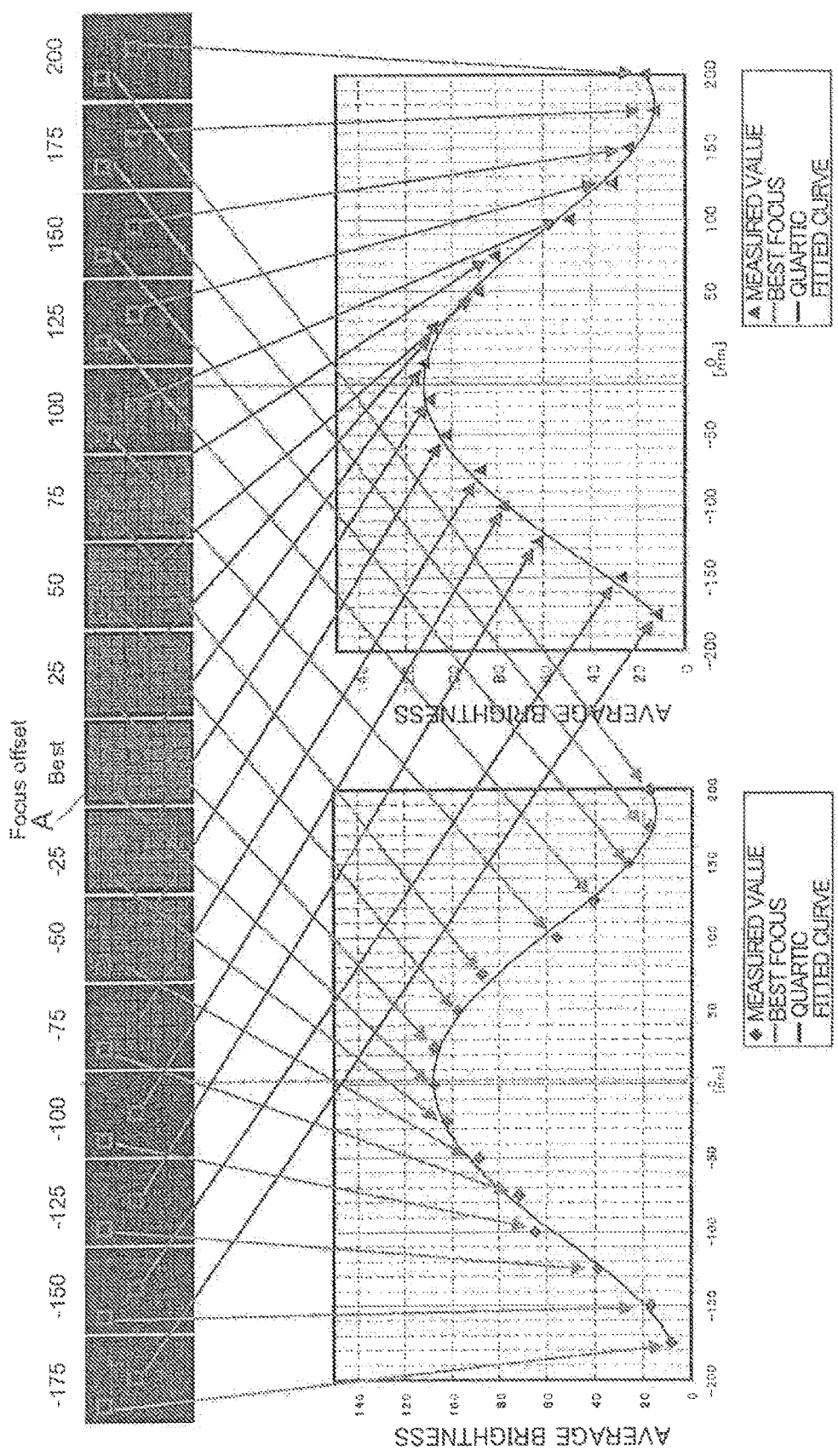
FIG. 10 shows an example of a focus curve.

As shown in FIG. 10, the image processing section 40 finds the focus curve, that is, the graph showing a relationship between the average brightness in the setting area A of the same position in each shot (different in focus offset from each other) and the corresponding focus offset, for each setting area A having found the average brightness (step S106). After finding the focus curve, the image processing section 40 finds a fitted curve for the focus curve, respectively (step S107). According to the knowledge of the present inventors, it is possible to utilize a fourth-order function for the fitted curve. Further, the focus curve found here is referred to as the reference focus curve. It is possible to use any other functions for the fitted curve (for example, third-order function), as a fitting function.

Figure 11:
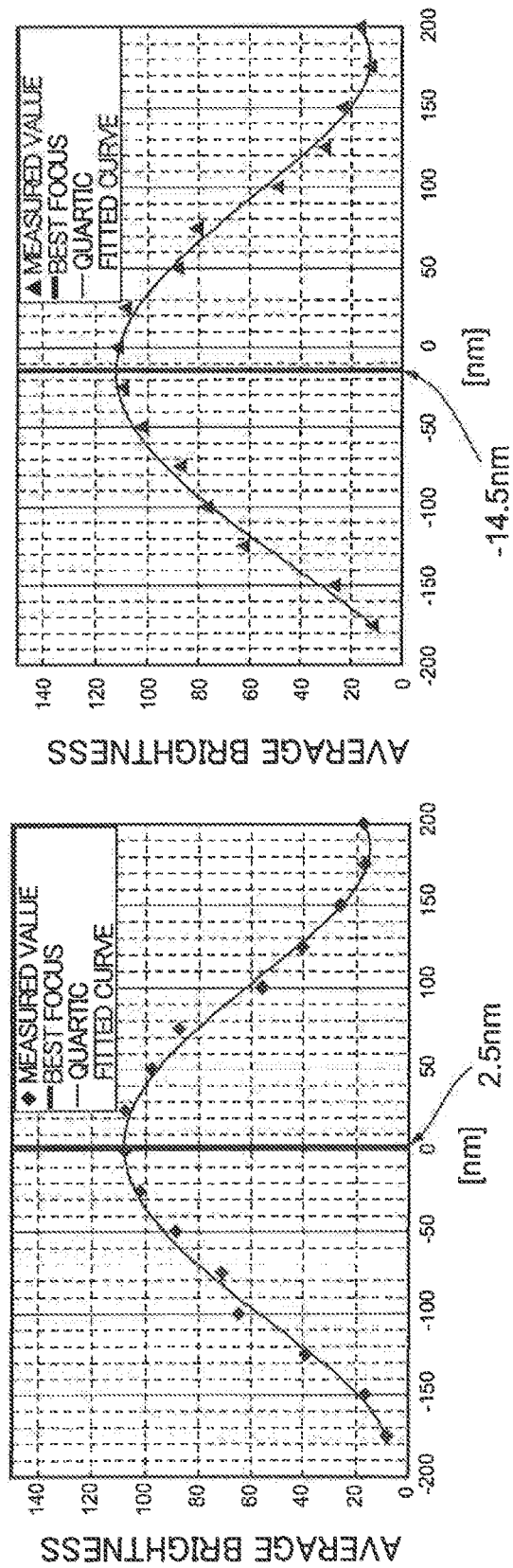
FIGS. 11A and 11B are graphs showing a relationship between the focus curve and the best focus.
Figure 12:
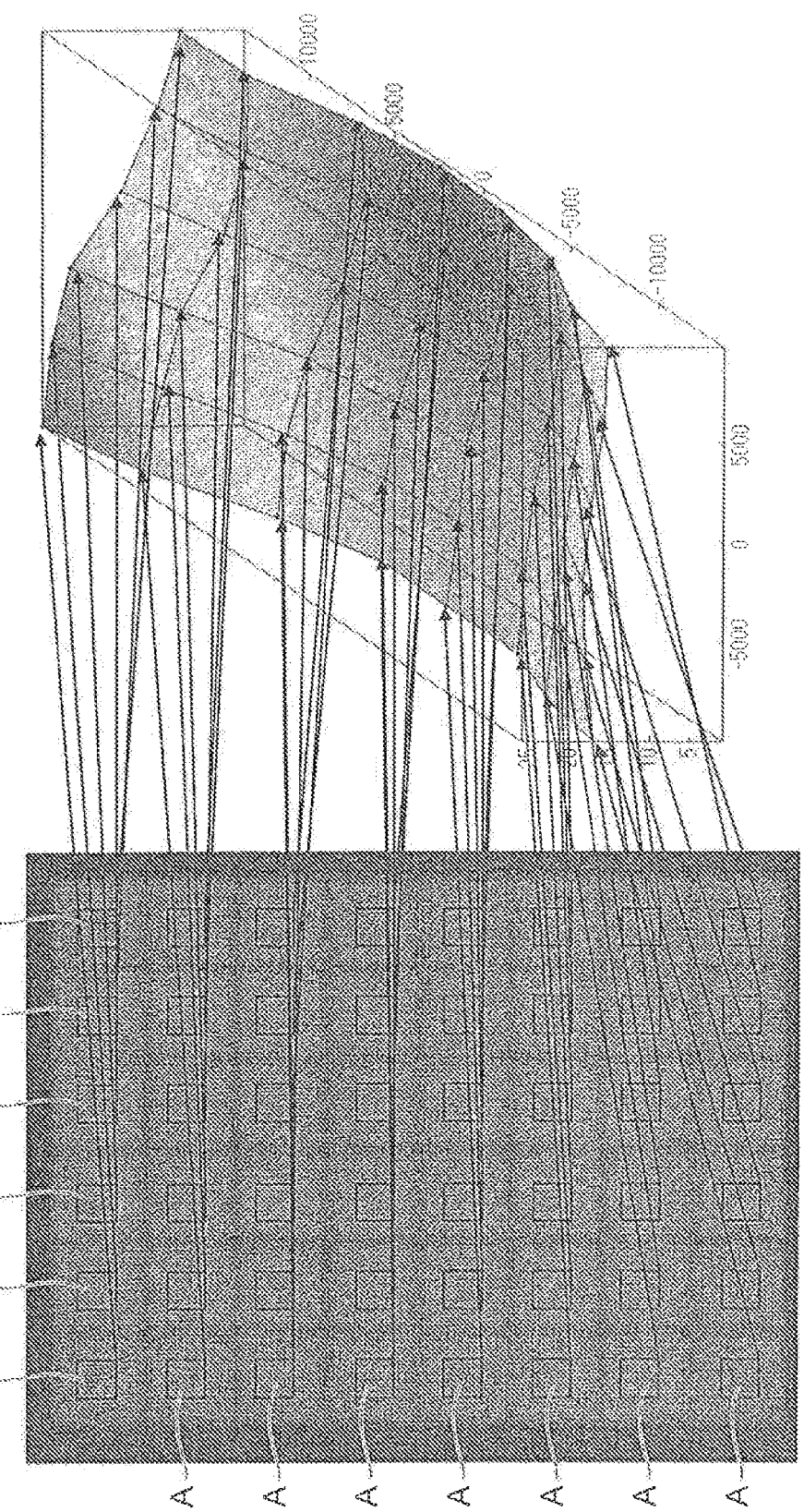
FIG. 12 shows a distribution of the focus offset within a shot.

Next, the image processing section 40 finds the focus offset for the average brightness to become (local) maximal on the approximate focus curve (step S108). For example, in the case of the focus curve shown in FIG. 11A, the focus offset for the average brightness to become maximum is 2.5 nm. Further for example, in the case of the focus curve shown in FIG. 11B, the focus offset for the average brightness to become maximum is −14.5 nm. At this time, the image processing section 40 finds the focus offset for the average brightness to become maximum for each setting area A (step S109). In so doing, as shown in FIG. 12, it is possible to find a distribution of the focus offset for the average brightness of diffracted light to become maximum in the shot.

By virtue of this, based on the distribution of the focus offset in the shot for the average brightness of diffracted light to become maximum, it is possible to (approximately) find the inclination of the focus offset of the slit (light) exposed by the exposure device 101 in the long-side direction (that is, the inclination amount of image plane), and the inclinations of the focus offset of the reticle stage and wafer stage of the exposure device 100 in the scanning direction, respectively. Even though the focus offset for the average brightness of diffracted light to become maximum is not the best focus, the relationship is substantially same between the focus offset and the average brightness of diffracted light because the pattern in the shot is analogous respectively, and the inclination of the image plane lies in a relative positional relation of each imaging point. Thereby, it is possible to find the inclination of the image plane by finding the maximal value of the average brightness. The inclination of the image plane found in this manner is outputted to the exposure device 100 from the image processing section 40 via the signal output portion (not shown) after converted into parameters acceptable by the exposure device 100 such as image field curvature, maximum and minimum values, the diagonal inclination and the like. These obtained parameters are reflected to the exposure by the exposure device 100. Further, the inclination of the image plane in the embodiment refers to the comprehensive inclination of the image plane with respect to the photoresist layer on the wafer due to the image plane inclination of the projection image by the projection lens in the exposure device 100, and the motion error of the reticle stage and the wafer stage.

Figure 13:
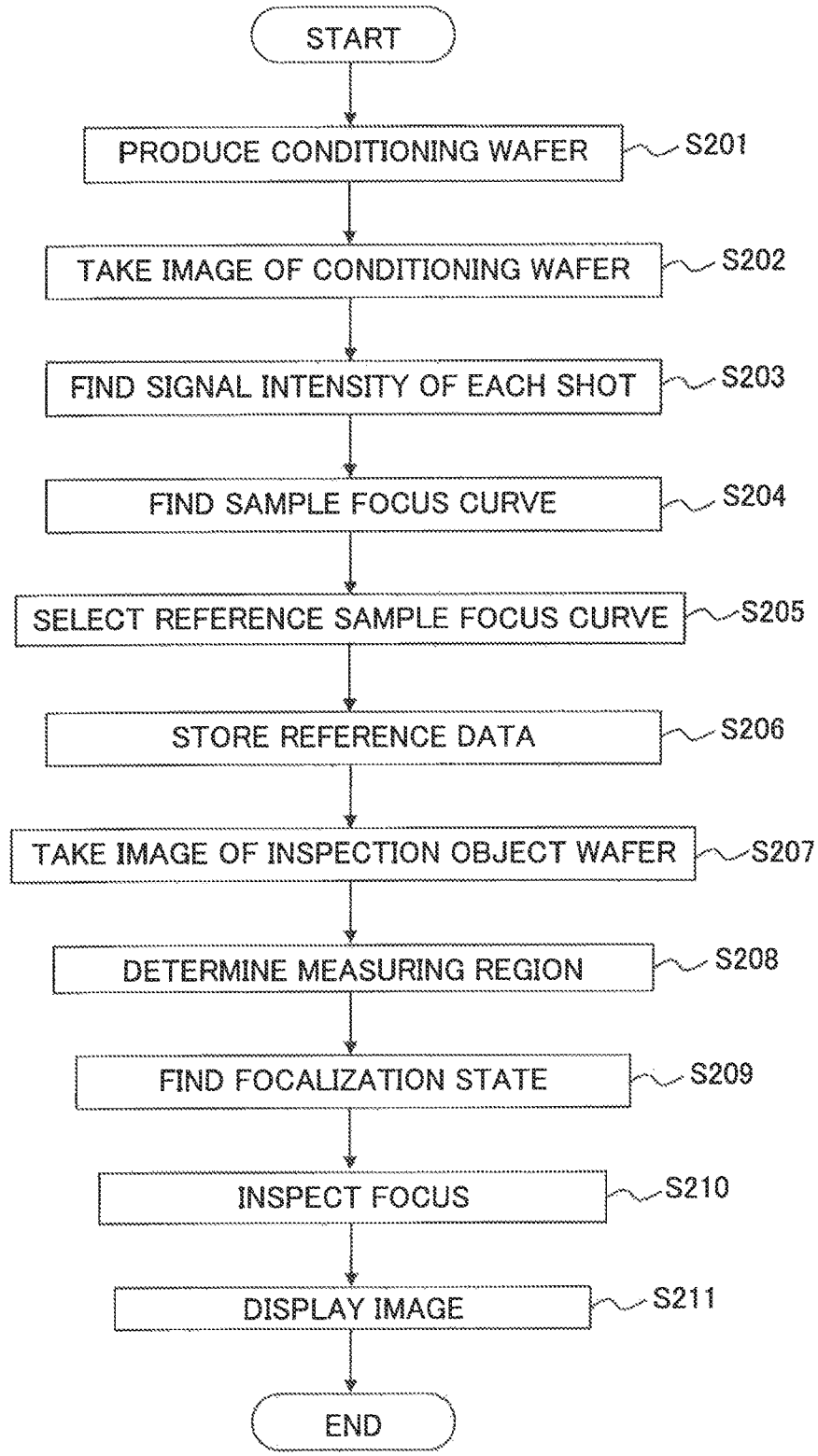
FIG. 13 is a flowchart showing a method for finding a focusing state in exposure due to the exposure device.

Further, the image processing section 40 is configured to be capable of finding the focusing state in exposure by the exposure device 100 from the diffraction image of the inspection object wafer 10, more specifically, the focusing variation state of the exposure device 100 for the entire surface of the wafer 10. Hereinbelow, referring to the flowchart shown in FIG. 13, explanations will be made with respect to a method for finding the focusing state in exposure by the exposure device 100. First, the image processing section 40 changes the focus offset and dose (exposure amount) of the exposure device 100 to matrix form to produce a condition-parameterizing wafer 10b with the repetitive pattern formed (see FIG. 14; step S201). At this time for example, the process of exposure and development is carried out by taking the central exposure shot of the condition-parameterizing wafer 10b as the best focus and best dose and changing the focus offset for each exposure shot aligning in the horizontal direction, while changing the dose for each exposure shot aligning in the vertical direction.

After producing the condition-parameterizing wafer 10b, the diffraction image of the condition-parameterizing wafer 10b is taken and obtained (step S202). In order to take the diffraction image of the condition-parameterizing wafer 10b, in the same manner as in the case of the diffraction inspection, first, the condition-parameterizing wafer 10b is carried onto the inspection stage 5. Next, the illumination system 20 irradiates the surface of the condition-parameterizing wafer 10b with the illumination light beam, and the imaging device 35 photoelectrical converts the diffraction image of the condition-parameterizing wafer 10b to generate an image signal and output the image signal to the image processing section 40. Then, based on the image signal of the condition-parameterizing wafer 10b inputted from the imaging device 35, the image processing section 40 generates a diffraction image of the condition-parameterizing wafer 10b. At this time, with respect to a plurality of pattern pitches, a plurality of illumination wavelengths, a plurality of light incoming angles and outgoing angles, i.e., a plurality of diffraction conditions, diffraction images of the condition-parameterizing wafer 10b are taken and obtained, respectively.

Further, when there are lower layers or lower layers unevenness in the repetitive pattern of the condition-parameterizing wafer 10b, it is possible to make it reduce the affect from the lower layers by utilizing a short-wavelength illumination light beam (for example, 248 nm, 313 nm and the like). Further, it is also possible to make it reduce the affect from the lower layers by inserting the illumination-side polarizing filter 26 setting the transmission axis in a predetermined azimuth into the optical path such that an s-polarized light beam is obtained as the illumination light. Further, it is still possible to make it reduce the affect from the lower layers by inserting the light-receiving-side polarizing filter 32 setting the transmission axis in a predetermined azimuth into the optical path such that only the s-polarized diffraction light beam can be received.

After taking the diffraction images of the condition-parameterizing wafer 10b, the image processing section 40 finds the signal intensity of each shot according to each diffraction image obtained under the plurality of diffraction conditions, respectively (step S203). At this time, the average signal intensity in the same shot is taken as the signal intensity of each shot. By virtue of this, it is possible to eliminate the influence of image plane inclination.

Next, the image processing section 40 finds the focus curve (to be referred to as the sample focus curve hereinbelow as appropriate to distinguish it from the reference focus curve found in measuring the image plane inclination), for each different dose with respect to the diffraction image taken respectively under the plurality of diffraction conditions (different diffraction orders or different wavelengths; step S204). The sample focus curve is a graph showing a relationship between the signal intensity of each shot and the corresponding focus offset (identical in dose but different in focus offset from each other). By virtue of this, for each different dose, it is possible to find a plurality of sample focus curves corresponding to the plurality of diffraction conditions, respectively. Further at this time, in the same manner as in the case of the reference focus curve, fitted curves are also found for the sample focus curves, respectively. According to the knowledge of the present inventors, it is possible to utilize a fourth-order function for the fitted curves. It is possible to use any other functions for the fitted curve (for example, third-order function), as a fitting function.

Next, the image processing section 40 selects at least two sample focus curves utilized to find the focusing state in exposure from the plurality of sample focus curves (step S205). At this time for example, three kinds of sample focus curves are selected and determined to correspond to the diffraction conditions little affected by dose and lower layers variations (to be referred to as the reference sample focus curves hereinbelow as appropriate to distinguish them from other sample focus curves). In order to select and determine three kinds of reference sample focus curves, first, the image processing section 40 extracts a plurality of sample focus curves sensitive to focus variation from a plurality of sample focus curves. Next, the image processing section 40 extracts a plurality of sample focus curves less sensitive to dose variation from the sample focus curves sensitive to focus variation. Then, the image processing section 40 selects and determines three sample focus curves different from each other in curve peak or bottom position (focus offset) from the sample focus curves sensitive to focus variation but less sensitive to dose variation as the reference sample focus curves.

Figure 14:
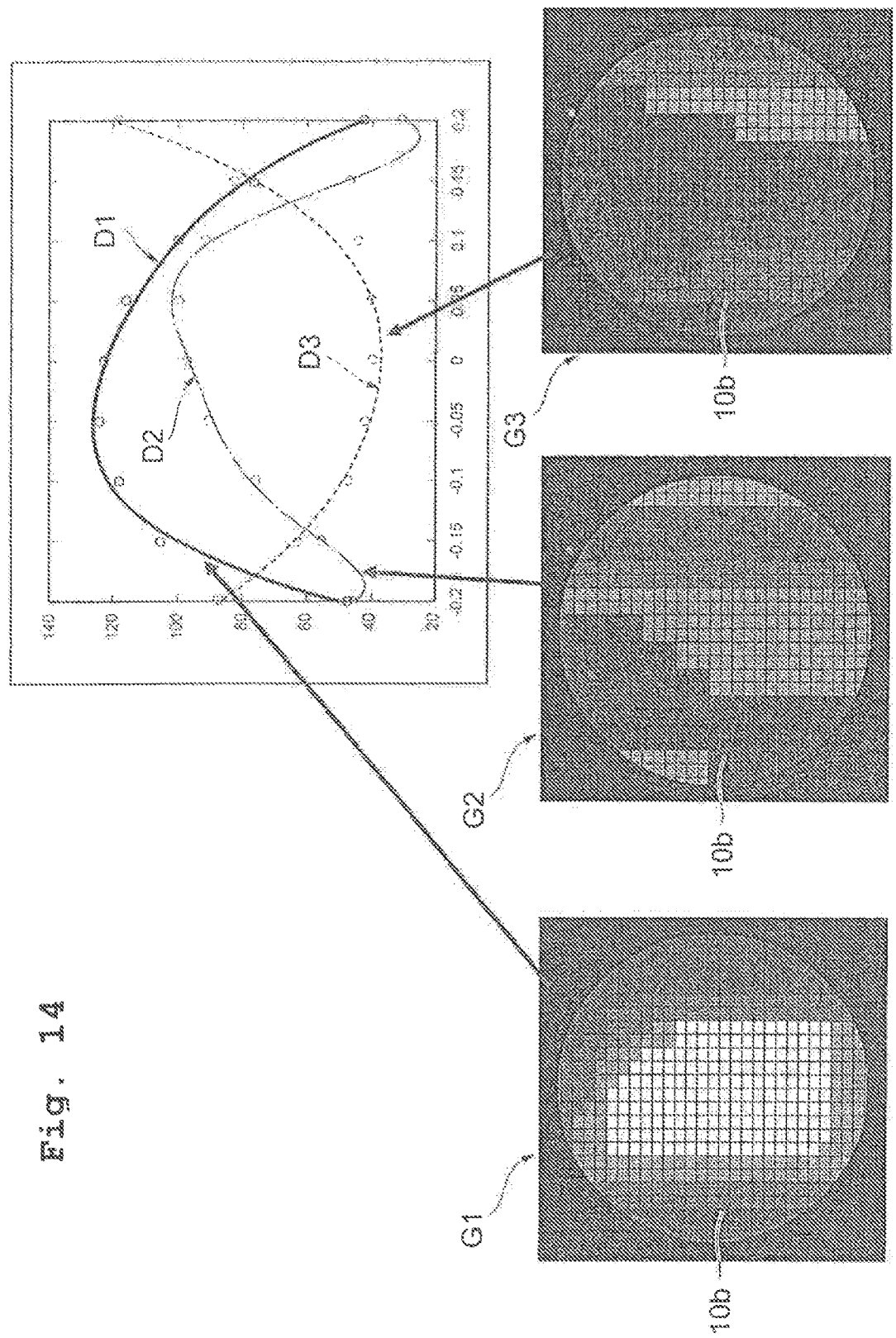
FIG. 14 shows diffraction images of a condition-parameterizing wafer taken under different conditions and focus curves.

By virtue of this, it is possible to find a diffraction condition little affected by dose and lower layers variations, and three reference sample focus curves corresponding to the diffraction condition. FIG. 14 shows examples of the reference sample focus curves found in this manner. FIG. 14 shows three reference sample focus curves D1 to D3, as well as diffraction image G1 for obtaining the first reference sample focus curve D1, diffraction image G2 for obtaining the second reference sample focus curve D2 and diffraction image G3 for obtaining the third reference sample focus curve D3, respectively. Further, each of the diffraction images G1 to G3 shown in FIG. 14 is that of the condition-parameterizing wafer 10b taken by changing the pattern pitch or illumination wavelength and with the same order of diffracted light (first-order diffracted light). Further, each diffraction image may as well be taken by only changing the order of diffracted light and with the same pattern pitch, illumination wavelength, and the like.

After selecting and determining three reference sample focus curves, the image processing section 40 outputs the data with respect to the equation for the approximate curves of the determined reference sample focus curves to the storage section 45 to be stored as reference data (step S206). Further, being not limited to the equation for the fitted curves of the reference sample focus curves, the image processing section 40 may as well output a data map showing a relationship between the signal intensity and the focus offset found from the equation for the fitted curves to the storage section 45 to be stored as the reference data.

Further, when there are a plurality of exposure devices 101, then even for exposure devices 101 of the same type, the NA (numerical aperture) may still be different for each device and for each switchable illumination conditions. Therefore, the reference data may be found for each exposure device or for each illumination condition, and may be stored into the storage section 45.

After the storage section 45 stores the reference data with respect to the three reference sample focus curves, the image processing section 40 obtains diffraction images of the inspection object wafer 10 (step S207). At this time, the diffraction images of the wafer 10 are obtained for the same three diffraction conditions as those for obtaining the reference sample focus curves, respectively.

After obtaining the diffraction images of the inspection object wafer 10, the image processing section 40 determines whether or not the region corresponding to each pixel is a measuring region in the shot based on the signal intensity of each pixel of the diffraction images (step S208), and excludes pixels corresponding to streets and the like from the measuring object.

After determining whether or not the region corresponding to each pixel is a measuring region in the shot, the image processing section 40 finds the focus variation state of the exposure device 100 with respect to the surface of the wafer 10 from the diffraction images of the inspection object wafer 10 (step S209). At this time, the focus offset of the exposure device 100 with respect to the surface of the wafer 10 for each predetermined pixel (in the unit of a single pixel or multiple pixels) is found based on the signal intensity of the diffraction images of the wafer 10 by utilizing the reference data stored in the storage section 45 (that is, the equation for the approximate curves of the reference sample focus curves or the data map). Further, in the case of finding the focus offset in the unit of multiple pixels, it is also necessary to distinguish the shot-induced defocus from the defocus due to foreign substances. Therefore, the region for finding the focus offset may be smaller than one shot (1/10 thereof, for example).

Figure 15:
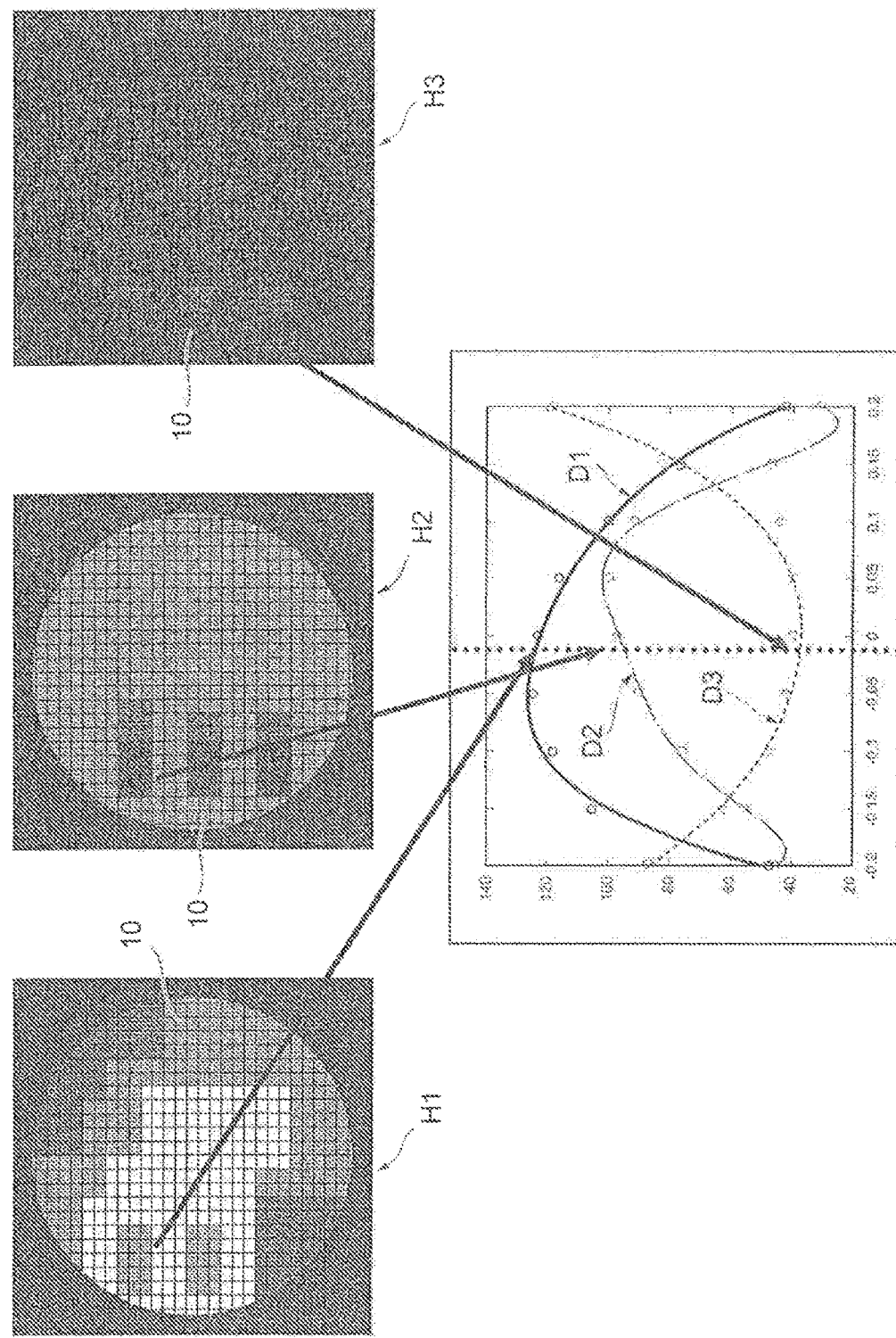
FIG. 15 shows a method for finding the focus offset from the diffraction images of a wafer taken under different conditions.

When finding the focus offset, since the storage section 45 stores the function (or data map) for the fitted curves of the reference sample focus curves corresponding respectively to three diffraction conditions, it is possible to find the focus offset, respectively, for each predetermined pixel based on the signal intensity of the diffraction images of the wafer 10 obtained respectively under the same condition. Further, because the focus curves are curve lines, a plurality of candidates of focus offset (possibly one, according to the condition) are calculated from the signal intensity of one diffraction image. On the other hand, by utilizing three reference sample focus curves D1 to D3 different from each other in curve peak or bottom position (focus offset), as shown in FIG. 15, the focus offset to be calculated is determined to be one. For example, the focus offset is found such that the square sum of the difference between the signal intensity under each condition and the approximate curve corresponding to that condition may become minimal. Further, focus offset may as well be adopted with a dose for the minimum square sum of the difference by preparing three reference sample focus curves D1 to D3 on each different dose. Further, the signal intensity may as well be weighted under the condition of relatively steep curve slope (that is, relatively high sensitivity to focus change). Further, with respect to pixels for which the minimum square sum of the difference exceeds a predetermined value, as an abnormal value, the result may as well not be adopted.

By virtue of this, it is possible to calculate the focus offset for each pixel on the entire surface of the wafer 10, as well as to determine the focus variation state of the exposure device 100 at each position of the surface of the wafer 10. Further, FIG. 15 shows three reference sample focus curves D1 to D3, as well as diffraction image H1 of the wafer 10 taken under the diffraction condition for obtaining the first reference sample focus curve D1, diffraction image H2 of the wafer 10 taken under the diffraction condition for obtaining the second reference sample focus curve D2, and diffraction image H3 of the wafer 10 taken under the diffraction condition for obtaining the third reference sample focus curve D3, respectively.

Figure 16:
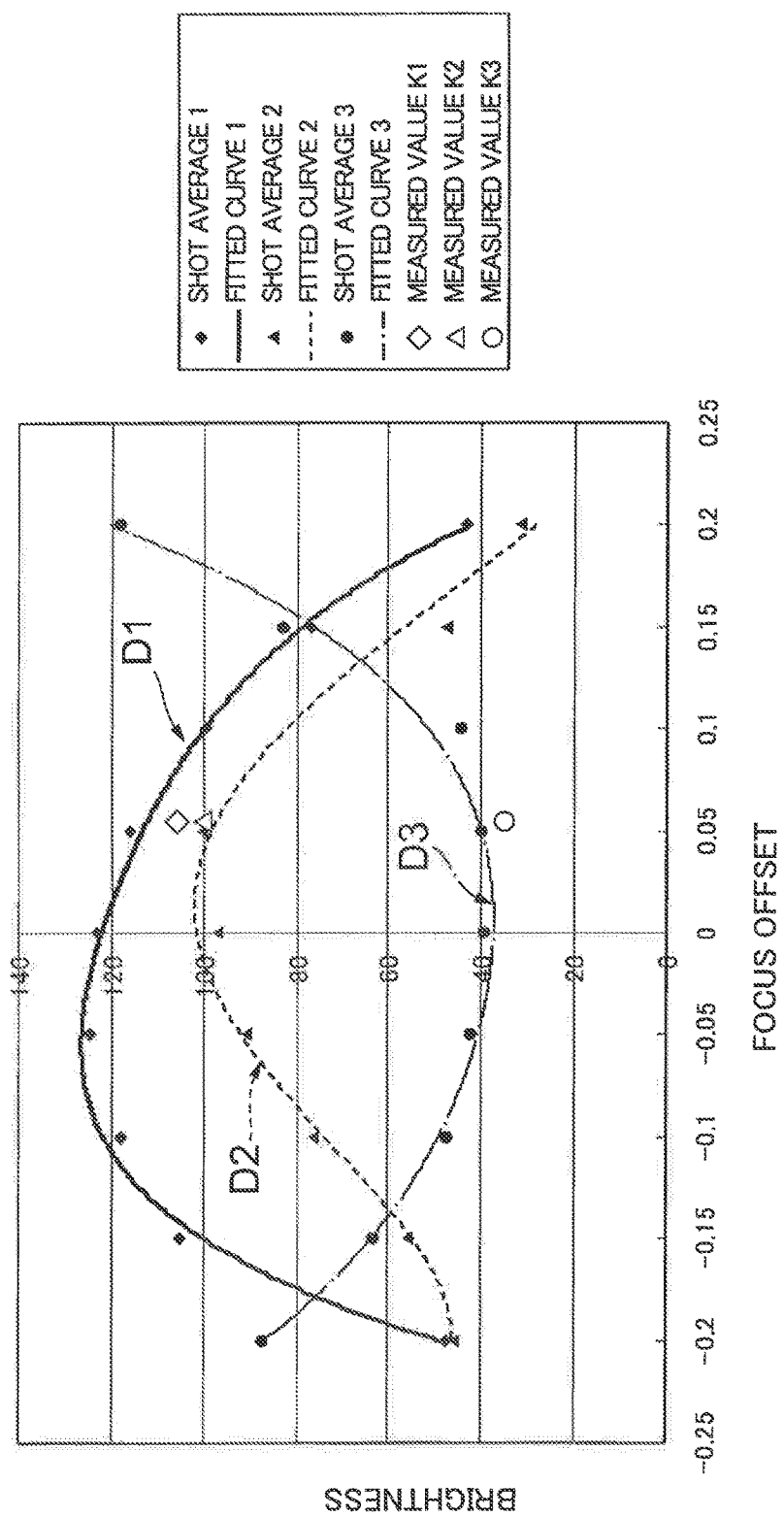
FIG. 16 is a graph showing a relationship between the focus curve and a measuring value of signal intensity.

Further, FIG. 16 shows a relationship between the reference sample focus curves D1 to D3 and the measuring value of each signal intensity of the focus offset for the minimum square sum of the difference (the first signal intensity K1, the second signal intensity K2 and the third signal intensity K3). It could be understood from FIG. 16 that there are high consistencies between the first detection signal (the first signal intensity K1) according to the diffracted light proceeding in the first direction from the repetitive pattern 12 detected by the imaging device 35 and the first reference data corresponding to this diffraction condition (the first reference sample focus curve D1), between the second detection signal (the second signal intensity K2) according to the diffracted light proceeding in the second direction from the repetitive pattern 12 and the second reference data corresponding to this diffraction condition (the second reference sample focus curve D2), and between the third detection signal (the third signal intensity K3) according to the diffracted light proceeding in the third direction from the repetitive pattern 12 and the third reference data corresponding to this diffraction condition (the third reference sample focus curve D3), respectively.

After finding the focus offset for each pixel on the entire surface of the wafer 10, the inspection section 50 inspects whether or not the found focus offset (focusing state) is abnormal (step S210). At this time, for example, the inspection section 50 determines it to be normal when the found focus offset is within the range of a predetermined threshold value, or abnormal when the found focus offset is out of the range of the predetermined threshold value.

Figure 17:
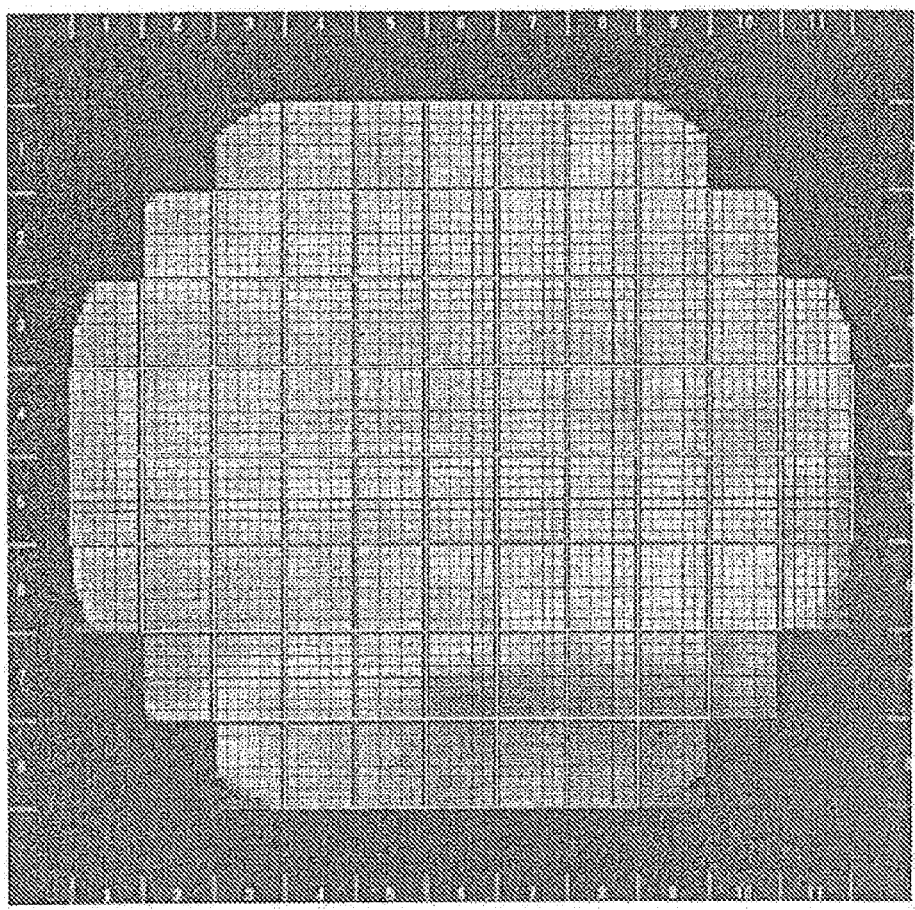
FIG. 17 shows a variation state of focus with respect to the wafer surface.

After inspecting whether or not the focus offset is abnormal, the image processing section 40 generates an image for the wafer 10 having converted the focus offset found for each pixel into the signal intensity with each corresponding pixel, and displays the image with the inspection result of the focus offset and the like on the image display device (not shown) (step S211). Further, being not limited to the surface inspection apparatus 1 of the embodiment, it is also possible to utilize an image display device provided outside the inspection apparatus (for example, in the control room of a semiconductor production line and the like) and connected to the inspection apparatus. Here, FIG. 17 shows an example of the image of the wafer 10 having converted the focus offset into signal intensity. Further, the image shown in FIG. 17 is not limited to a black and white image but may as well be displayed in color.

In this manner, according the surface inspection apparatus 1, the image processing section 40 determines the focusing state in exposure (processing condition) for the repetitive pattern 12 in the wafer 10 based on the consistency between the first detection signal (the first signal intensity K1) detected by the imaging device 35 and the first reference data (the first reference sample focus curve D1), the consistency between the second detection signal (the second signal intensity K2) and the second reference data (the second reference sample focus curve D2), and the consistency between the third detection signal (the third signal intensity K3) and the third reference data (the third reference sample focus curve D3). By virtue of this, it is possible to find the focusing state in exposure based on the image of the wafer 10 exposed with a mask pattern utilized for actual exposure.

In this manner, when the surface inspection apparatus 1 carries out surface inspection on the wafer 10, the image processing section 40 of the surface inspection apparatus 1 outputs the information about the found focus variation state (focus offset) of the exposure device 100 with respect to the surface of the wafer 10 to the exposure device 100 (the main control device 200). Then, the main control device 200 of the exposure device 100 corrects various setting parameters about the focalization of the exposure device 100 based on the focus variation state of the exposure device 100 inputted from the surface inspection apparatus 1 such that the focusing state of the exposure device 100 becomes constant with respect to the surface of the wafer 10.

According to the exposure system 100 of such type, because the focus setting of the exposure device 100 is corrected according to the focusing state in exposure inputted from the surface inspection apparatus 1, it is possible to measure the focusing state in exposure in a short time with a high precision. Therefore, the correction can be made based on the focusing state of a higher precision, thereby allowing the focus of the exposure device 100 to be set more properly.

Figure 18:
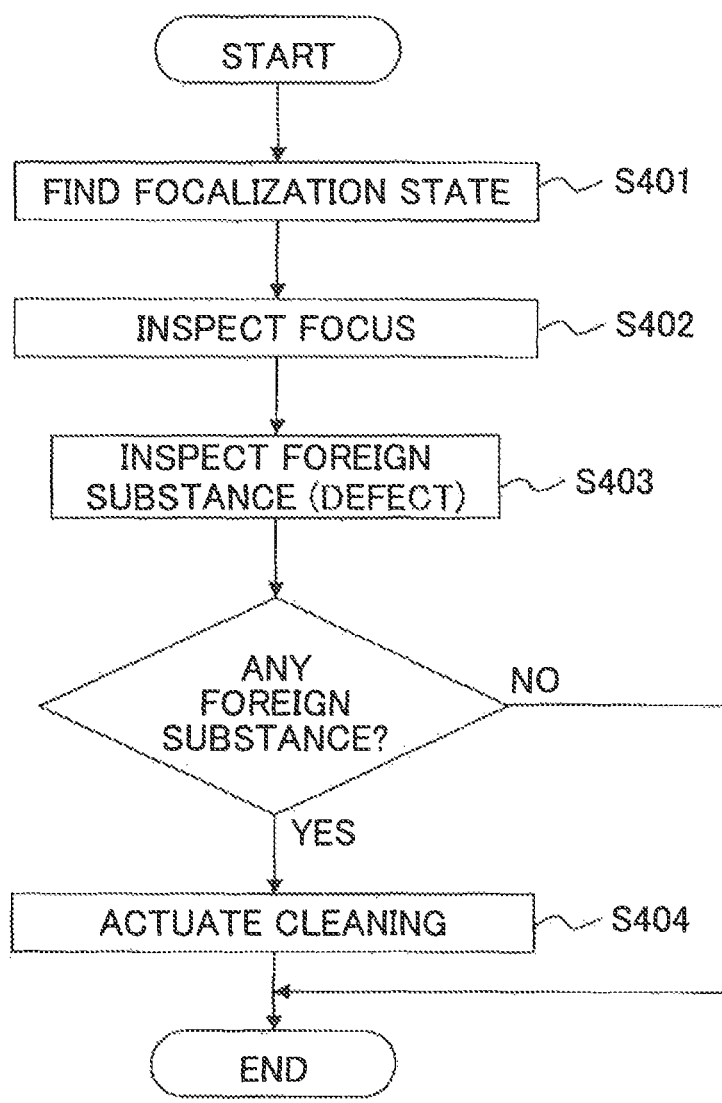
FIG. 18 is a flowchart showing a method for determining whether or not any foreign substance adheres to a wafer supporting surface as to affect an exposure result.

Further, the main control device 200 of the exposure device 100 determines whether or not to clean the wafer supporting surface of the wafer holder 153 with the cleaning device 160 based on the inspection result inputted from the surface inspection apparatus 1 as to whether or not there is any abnormity in focus value of the exposure device 100. Hereinbelow, referring to the flowchart shown in FIG. 18, explanations will be made with respect to a method (an exposure stage inspection method) for determining whether or not to clean the wafer supporting surface based on the inspection result by the surface inspection apparatus 1.

Figure 19A:
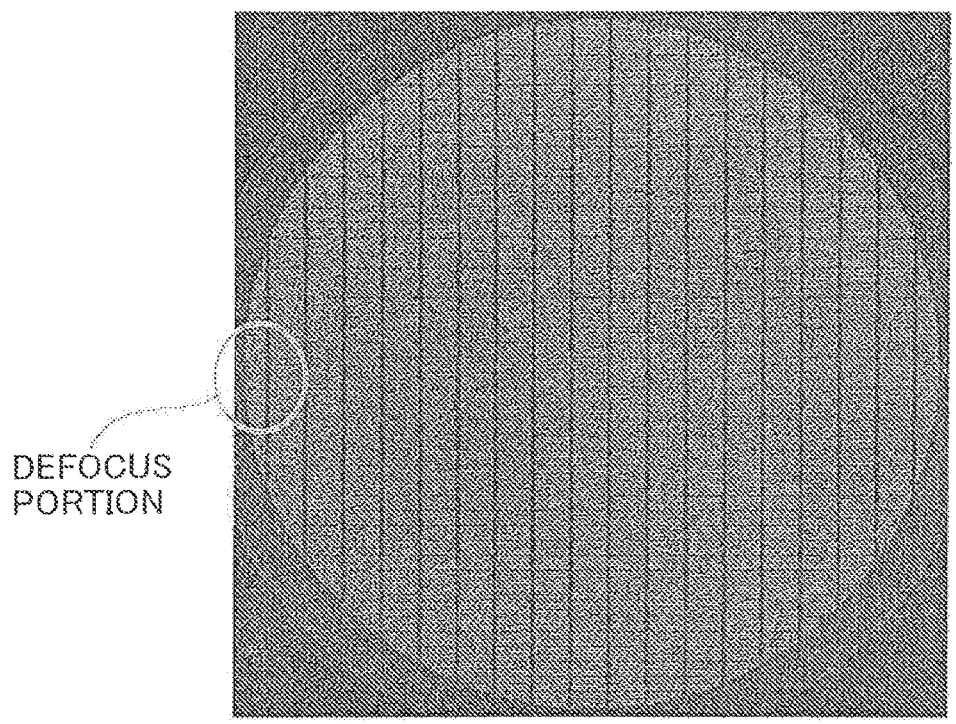
FIG. 19A shows an example of a localized defocus state (an image due to diffracted light) with respect to the wafer surface due to the influence of the foreign substance adhering to the wafer supporting surface.
Figure 19B:
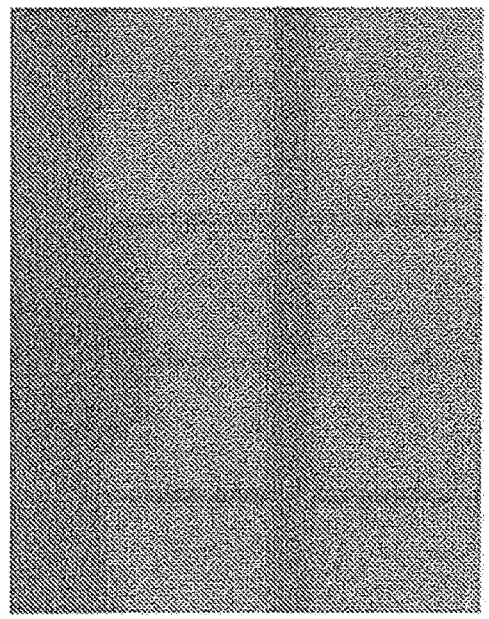
FIG. 19B is an enlarged view of the defocus portion in FIG. 19A.

First, as described hereinbefore, the surface inspection apparatus 1 finds the focusing state in exposure based on the images of the wafer 10 exposed with the mask pattern utilized in actual exposure (step S401), and inspects whether or not there is any abnormity in focus value from the focusing state (step S402). Here, when minute foreign substances such as resist residue and the like adhere to the wafer supporting surface of the wafer holder 153, then as shown in FIGS. 19A and 19B for example, carrying out exposure with the wafer 10 held thereon causes the focus value to be defocused in the direction of upholding the wafer 10 due to the influence of the foreign substances only in the place of the existing foreign substances.

Then, based on the inspection result of the focus value, the main control device 200 determines whether or not there is any defect in the wafer supporting surface of the wafer holder 153, that is, whether or not there are any foreign substances adhering thereto (step S403). When the focus value is determined to be abnormal (out of the range of a predetermined threshold value) locally on the surface of the wafer 10 (for example, only a few pixels corresponding to ⅒ of one shot) because defocus occurs only in the place of existing foreign substances in the direction of upholding the wafer 10 due to the influence of the foreign substances as described hereinabove, then it is possible to determine that there are some foreign substances adhering to the wafer supporting surface of the wafer holder 153 and, furthermore, to specify the position of the adhering foreign substances on the wafer supporting surface of the wafer holder 153 (to be referred to as the foreign substance adhesion position hereinbelow). Further, when the focus value is determined to be abnormal in one entire shot of the wafer 10, then not the influence due to the adhesion of foreign substances but other causes (such as shot-induced defocus due to AF error and the like) are determined; thereby, the cleaning device 160 does not carry out the aftermentioned cleaning of the wafer supporting surface of the wafer holder 153.

When the surface inspection apparatus 1 determines the focus value to be abnormal locally on the surface of the wafer 10, and some foreign substances adhere to the wafer supporting surface of the wafer holder 153, then the exposure device 100 carries out a cleaning operation on the wafer supporting surface (step S404). The main control device 200 controls the wafer stage drive device 151 to move the wafer stage 150 under the cleaning device 160. At this time, the wafer stage 150 is moved such that the foreign substance adhesion position on the wafer supporting surface of the wafer holder 153 is positioned underneath the cleaning device 160. Then, the main control device 200 controls the movement mechanism 162 via the cleaning control device 165 to cause the cleaning surface of the cleaning member 161 to contact with the wafer supporting surface of the wafer holder 153, while moving the cleaning member 161 relative to the wafer holder 153 in the X-Y plane. Further at this time, the main control device 200 controls the suction device 164 via the cleaning control device 165 to suck and eliminate the foreign substances on the wafer holder 153.

Further, the cleaning device 160 may as well clean the entire wafer supporting surface of the wafer holder 153 as its cleaning range. Alternatively, it may as well not clean the entire wafer supporting surface of the wafer holder 153, but only clean a predetermined range including the foreign substance adhesion position of the wafer supporting surface and, in so doing, it is possible to clean the necessary place only on the wafer supporting surface, thereby allowing for reduction of the time for returning to the exposure process.

In this manner, based on the inspection result from the surface inspection apparatus 1, the exposure device 100 can determine whether or not foreign substances adhering to the wafer supporting surface of the wafer holder 153 affect the exposure result for the wafer 10, that is, whether or not the foreign substances become the cause of focus error. Further, when the foreign substances are determined to be the cause of focus error, then the cleaning device 160 comes to clean the wafer supporting surface of the wafer holder 153. Thus, it is possible to clean the wafer supporting surface at a proper time without stopping the exposure process beyond necessity as done conventionally, thereby allowing for improvement in the yield rate of fabricating semiconductor elements.

Further, when the surface inspection apparatus 1 determines the focus value to be locally abnormal in the same place with a plurality of wafers 10, then the main control device 200 may as well determine that foreign substances adhere to the wafer supporting surface of the wafer holder 153. In so doing, it is possible to determine the adhesion of foreign substances to the wafer supporting surface of the wafer holder 153 in a further correct manner.

Further, when the surface inspection apparatus 1 determines the focus value to be locally abnormal in the circumferential portion of the wafer 10, then the main control device 200 may as well determine that foreign substances adhere to the wafer supporting surface of the wafer holder 153. That is, the range for the main control device 200 to determine presence or absence of foreign substances may as well be restricted to the circumferential portion of the wafer (for example, a range of a few millimeters from the circumferential edge of the wafer 10). With an immersion exposure device such as the exposure device 100 of the embodiment, there are many cases that foreign substances in the vicinity of the circumferential portion of the wafer come around behind the back side of the wafer in exposure due to the influence of liquid, and stand between the circumferential portion of the wafer and the wafer holder 153 (see FIGS. 19A and 19B). Therefore, by restricting the range for determining presence or absence of foreign substances to the circumferential portion of the wafer, it is possible to determine the adhesion of foreign substances to the wafer supporting surface of the wafer holder 153 in a more efficient manner. Further, in order to determine presence or absence of foreign substances, it is still possible to carry out a more efficient determination, without finding the focusing state (focus offset) of the entire wafer, by finding the focusing state (focus offset) in the place of either less than or greater than a predetermined signal from an image of the entire wafer due to the diffracted light such as shown in FIGS. 19A and 19B.

Next, referring to the flowchart shown in FIG. 20, explanations will be made with respect to a method for producing a semiconductor device utilizing the exposure device 100 including such kind of exposure stage inspection system. The semiconductor device (not shown) is produced through a design process for designing the function and performance of the device (step S301), a reticle production process for producing a reticle based on the design process (step S302), a wafer production process for producing a wafer from a silicon material (step S303), a lithography process for transferring a reticle pattern to the wafer by exposure and the like (including an exposure process, a development process and the like; step S304), an assembly process for assembling the device (including a dicing process, a bonding process, a packaging process and the like; step S305), an inspection process for inspecting the device (step S306), and the like.

In the method of the present embodiment for producing a semiconductor device, the exposure system 100 including the aforementioned exposure stage inspection system is utilized to carry out the exposure of the pattern, in the lithography process. That is, as described hereinbefore, after the exposure device 100 carries out the exposure process, through the development process by the development device (not shown) and the like, the surface inspection apparatus 1 carries out the surface inspection on the wafer 10 with the repetitive pattern 12 formed in its surface. At this time, the surface inspection apparatus 1 determines the focusing state in exposure, based on which it is possible to determine whether or not the foreign substance adhering to the wafer supporting surface of the wafer holder 153 affects the exposure result of the wafer 10, that is, whether or not that foreign substance is the cause of focus error. Then, when the foreign substance is determined to be the cause of focus error, the cleaning device 160 performs a cleaning of the wafer supporting surface of the wafer holder 153. Since the cleaned wafer holder 153 on the surface of which the foreign substance has been removed can be utilized in the subsequent exposure process, it is possible to prevent from producing defective products. Accordingly, it is possible to perform the cleaning of the wafer supporting surface of the wafer holder 153 at an appropriate timing without stopping the exposure process beyond necessity as in the conventional case, thereby allowing the semiconductor device to be produced with high productivity.

In the above surface inspection apparatus 1, although the focusing state in exposure (processing condition) for the repetitive pattern 12 in the wafer 10 is determined by utilizing three kinds of reference data (reference sample focus curves D1 to D3), the present teaching is not limited to this. For example, two or five kinds of reference data may as well be utilized. The focusing state in exposure may be determined by utilizing at least two kinds of reference data opposite in the manner of change of the detection signal with respect to focus variation.

In the above surface inspection apparatus 1, although inspection is carried out on the repetitive pattern 12 formed through exposure in the resist film on the wafer 10, the present teaching is not limited to this. For example, inspection may as well be carried out on the pattern after etching. By virtue of this, not only the focusing state in exposure, but the defect (abnormity) in etching can also be detected.

Further, in the above surface inspection apparatus 1, in addition to the diffraction image of the condition-parameterizing wafer 10b, the polarization image of the condition-parameterizing wafer 10b may as well be utilized, by the same method as in the aforementioned case, to find a plurality of sample focus curves due to the polarized light for each different dose and, therefrom, select and determine a plurality of reference sample focus curves due to the polarized light. By virtue of this, the reference sample focus curves due to the polarized light (reference data) are utilized to find the focus variation state of the exposure device 100 with respect to the surface of the wafer 10 based on the signal intensity of the polarization image taken by the imaging device 35. In this case, because a number of detection conditions increase compared with the case of the diffraction image only, it is possible to measure the focusing state in exposure with a higher precision. Further, with the polarized light, because the focus offset can be considered to be the best focus as the signal intensity becomes maximal on the focus curve, it is possible to easily know the focus offset for the best focus.

Further, in the above surface inspection apparatus 1, although the focusing state in exposure with respect to the repetitive pattern 12 in the wafer 10 is determined by utilizing three kinds of reference data sensitive to focus variation but less sensitive to dose variation (the reference sample focus curves D1 to D3), the present teaching is not limited to this. It is also possible to determine the dose in exposure with respect to the repetitive pattern 12 in the wafer 10 by extracting a plurality of sample focus curves sensitive to dose variation but less sensitive to focus variation from a plurality of sample focus curves and utilizing these sample focus curves.

In the above embodiment, although the exposure device 100 of the liquid immersion type having the local immersion device 140 is used as the exposure device, the present teaching is not limited to this. The present teaching can be applicable to the non-liquid immersion type exposure device.

What is claimed is:

1. An inspection apparatus which inspects a substrate supporting portion configured to support a substrate during an exposure performed by an exposure apparatus, the apparatus comprising:
    a irradiation unit which is configured to irradiate, with an illumination light beam, a surface of the substrate on which a pattern has been formed by an exposure by the exposure device;
    a detecting unit which is configured to detect reflected light from a pattern in the irradiated surface;
    a focusing state computation unit which is connected to the detection unit and which is configured to determine a focusing state of the pattern of the substrate, based on a detection result of the reflected light beam detected by the detection unit; and
    an inspection unit which is connected to the focusing state computation unit and which is configured to inspect the substrate supporting portion based on the focusing state determined by the focusing state computation unit.

2. The inspection apparatus according to claim 1, wherein the inspection unit inspects a convex state of the substrate supporting portion or an interspace between the substrate supporting portion and the substrate.

3. The inspection apparatus according to claim 1, wherein the focusing state computation unit forms a mapping of the focusing state based on a focusing state of patterns of a plurality of regions.

4. The inspection apparatus according to claim 1, wherein the detection unit is configured to detect a first detection signal according to a first light beam proceeding in a first direction from the pattern in a predetermined region of the substrate, and a second detection signal according to a second light beam, from the pattern in the predetermined region of the substrate, proceeding in a second direction different from the first direction;
    the inspection apparatus further comprises a storing unit which is configured to store a first reference data indicating a relationship between the first detection signal detected by the detection unit and a plurality of predetermined processing conditions, and a second reference data indicating a relationship between the second detection signal detected by the detection unit and the plurality of predetermined processing conditions, using the substrate having a plurality of patterns processed under the plurality of predetermined processing conditions; and
    the focusing state computation unit determines the focusing state based on consistency between the first detection signal and the first reference data, and consistency between the second detection signal and the second reference data.

5. The inspection apparatus according to claim 1, wherein the inspection apparatus includes an illumination side polarization filter which is configured to filter an S-polarized light beam in the illumination light beam or a receiving side polarization filter which is configured to filter an S-polarized light beam in the first or second light beam, the illumination side polarization filter being provided to be removable in an optical path of the illumination light beam, and the receiving side polarization filter being provided to be removable in an optical path of the first or second light beam.

6. An exposure system comprising:
    the inspection apparatus as defined in claim 1;
    the exposure apparatus; and
    a transmission unit which is configured to transmit, from the inspection apparatus to the exposure device, an inspection result obtained by the inspection apparatus.

7. The exposure system according to claim 6, wherein the exposure apparatus is a liquid immersion type exposure apparatus which exposes the predetermined pattern onto the surface of the substrate via the liquid.

8. The exposure system according to claim 6, wherein the exposure apparatus includes a cleaning unit which is configured to clean the substrate supporting portion based on the inspection result of the inspection unit.

9. A maintenance system which maintains a substrate supporting portion configured to support a substrate during an exposure performed by an exposure apparatus, the maintenance system comprising:
    an irradiation unit which is configured to irradiate, with an illumination light beam, a surface of the substrate on which a pattern has been formed by an exposure by the exposure device;
    a detecting unit which is configured to detect reflected light from a pattern in the irradiated surface;
    a focusing state computation unit which is connected to the detection unit and which is configured to determine a focusing state of the pattern of the substrate, based on a detection result of the reflected light beam detected by the detection unit; and
    a cleaning unit which is configured to clean the substrate supporting portion of the exposure apparatus based on the determined the focusing state of the pattern of the substrate.

10. The maintenance system according to claim 9, wherein the focusing state computation unit forms a mapping of the focusing state based on a focusing state of patterns of a plurality of regions.

11. The maintenance system according to claim 9, wherein the detection unit is configured to detect a first detection signal according to a first light beam proceeding in a first direction from the pattern in a predetermined region of the substrate, and a second detection signal according to a second light beam, from the pattern in the predetermined region of the substrate, proceeding in a second direction different from the first direction;
    the maintenance system further comprises a storing unit which is configured to store a first reference data indicating a relationship between the first detection signal detected by the detection unit and a plurality of predetermined processing conditions, and a second reference data indicating a relationship between the second detection signal detected by the detection unit and the plurality of predetermined processing conditions, using the substrate having a plurality of patterns processed under the plurality of predetermined processing conditions; and
    the focusing state computation unit determines the focusing state based on consistency between the first detection signal and the first reference data, and consistency between the second detection signal and the second reference data.

12. The maintenance system according to claim 9, wherein the maintenance system includes an illumination side polarization filter which is configured to filter an S-polarized light beam in the illumination light beam or a receiving side polarization filter which is configured to filter an S-polarized light beam in the first or second light beam, the illumination side polarization filter being provided to be removable in an optical path of the illumination light beam, and the receiving side polarization filter being provided to be removable in an optical path of the first or second light beam.

13. An exposure system comprising:
   the maintenance system as defined in claim 9;
   the exposure apparatus; and
   a transmission unit which is configured to transmit, from the maintenance system to the exposure device, an inspection result obtained by the maintenance system.

14. The exposure system according to claim 13, wherein the exposure apparatus is a liquid immersion type exposure apparatus which exposes the predetermined pattern onto the surface of the substrate via the liquid.

\* \* \* \* \*